(12) United States Patent
Anderson et al.

(10) Patent No.: US 11,039,894 B2
(45) Date of Patent: Jun. 22, 2021

(54) ROBOTIC PORT PLACEMENT GUIDE AND METHOD OF USE

(71) Applicant: Verb Surgical Inc., Mountain View, CA (US)

(72) Inventors: Kent Anderson, Emerald Hills, CA (US); Katherine Anderson, Emerald Hills, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 271 days.

(21) Appl. No.: 15/959,137

(22) Filed: Apr. 20, 2018

(65) Prior Publication Data

US 2019/0321115 A1 Oct. 24, 2019

(51) Int. Cl.
*A61B 34/35* (2016.01)
*A61B 17/34* (2006.01)
*B25J 9/00* (2006.01)
*A61B 90/50* (2016.01)
*A61B 34/20* (2016.01)
(Continued)

(52) U.S. Cl.
CPC .............. *A61B 34/35* (2016.02); *A61B 5/062* (2013.01); *A61B 17/3423* (2013.01); *A61B 34/20* (2016.02); *A61B 90/50* (2016.02); *B25J 9/0009* (2013.01); *A61B 90/361* (2016.02); *A61B 2017/00477* (2013.01); *A61B 2034/2051* (2016.02); *A61B 2034/2055* (2016.02); *A61B 2034/305* (2016.02)

(58) Field of Classification Search
CPC ..... A61B 17/3423; A61B 34/35; A61B 90/50; A61B 34/20; A61B 5/062; A61B 90/361; A61B 2034/2051; A61B 2017/00477; A61B 2034/305; A61B 2034/2055; A61B 20/39; A61B 90/03; A61B 2090/3937; A61B 2090/3983; A61B 2090/395; A61B 2090/372; A61B 2090/3987; B25J 9/0009
See application file for complete search history.

(56) References Cited

U.S. PATENT DOCUMENTS 10,786,317 B2 9/2020 Zhou et al.
2012/0253515 A1* 10/2012 Coste-Maniere ...... A61B 34/70
700/250

(Continued)

FOREIGN PATENT DOCUMENTS

CN 104736097 A 6/2015

OTHER PUBLICATIONS

PCT Search Report and Written Opinion dated Jan 18, 2019, for related PCT Appln. No. PCT/US2018/030862 18 Pages.

(Continued)

*Primary Examiner* — George J Ulsh
*Assistant Examiner* — Andrew P. Restaino
(74) *Attorney, Agent, or Firm* — Womble Bond Dickinson (US) LLP

(57) ABSTRACT

A port placement guide may include a base, a member, and at least one tracking element. The base can be configured to couple to a surface of a patient at a preliminary port location for a robotic arm. The member can be coupled to the base and can comprise a first end and a second end opposite the first end. The at least one tracking element can be coupled to the member and can be configured to allow tracking of the member relative to the preliminary port location.

9 Claims, 18 Drawing Sheets

(51) Int. Cl.
  *A61B 5/06* (2006.01)
  *A61B 90/00* (2016.01)
  *A61B 17/00* (2006.01)
  *A61B 34/30* (2016.01)

(56) References Cited

U.S. PATENT DOCUMENTS

2013/0096570 A1* 4/2013 Solar ............... A61B 17/00234
                                                    606/108
2015/0141755 A1* 5/2015 Tesar .................. A61B 1/0676
                                                    600/111
2016/0089181 A1* 3/2016 Johnson ............. A61B 17/0218
                                                    600/424
2016/0113728 A1   4/2016 Piron et al.
2017/0231702 A1   8/2017 Crawford et al.
2018/0042686 A1* 2/2018 Peine .................... A61B 34/30

OTHER PUBLICATIONS

International Preliminary Report on Patentability for International Application No. PCT/US2018/030862 dated Oct. 29, 2020, 10 pages.

* cited by examiner

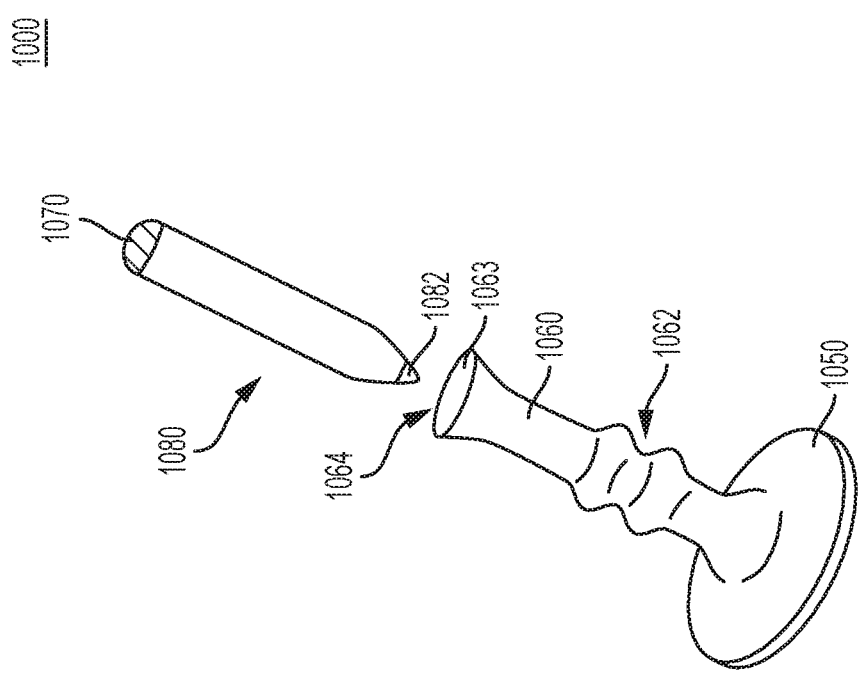

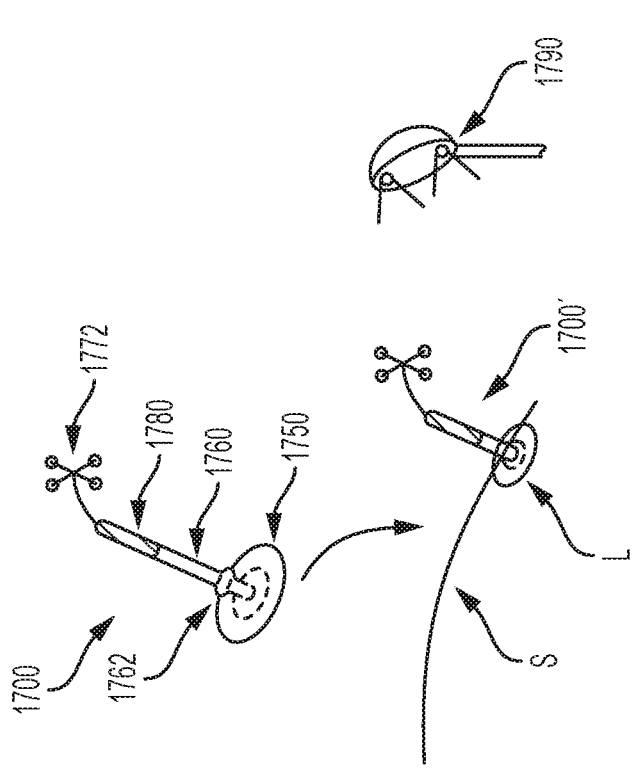
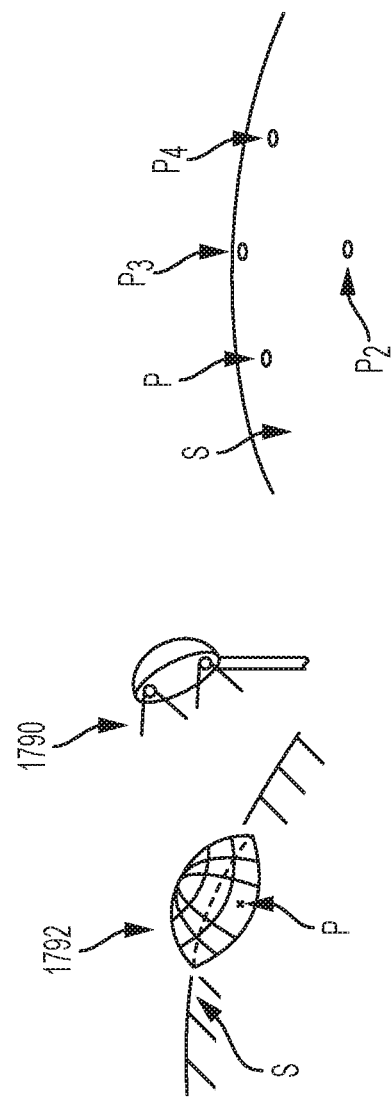
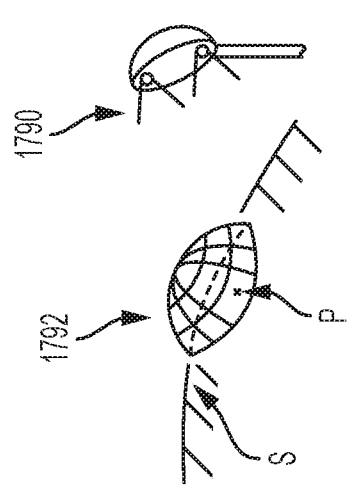
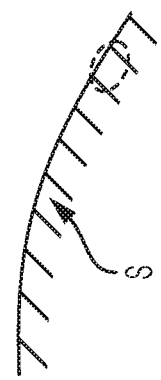
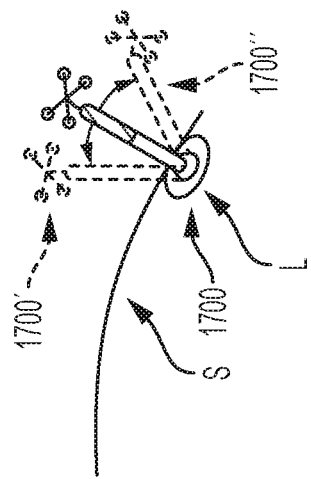

ROBOTIC PORT PLACEMENT GUIDE AND METHOD OF USE

FIELD

This invention relates generally to the field of robotic surgery, and more specifically to systems and methods for aiding port placement in robotic surgery.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. However, standard MIS systems have a number of drawbacks. For example, non-robotic MIS systems place higher demands on the surgeon, in part because they require surgeons to indirectly manipulate tissue via tools in a manner that may not be natural. Conventional robotic MIS systems, which may involve an operator viewing a display showing the endoscopic camera video feed and remotely operated to manipulate tools based on commands from an operator, may provide many benefits of MIS while reducing demands on the surgeon.

However, the locations of the incisions, or ports, in the patient are important to success of an MIS procedure, particularly those involving robotic MIS systems. For example, less-than-ideal locations of the incisions can affect access to the surgical worksite, increase risk of collisions and other interference between robotic arms, and/or may not be preferred for patient-specific needs, procedure-specific needs, and/or surgeon preferences.

Thus, it is desirable to be able to improve the process for determining effective port locations on a patient for a minimally-invasive surgical procedure.

SUMMARY

Systems and methods for guiding port placement on a patient and maneuvering a robotic arm toward the port location are described herein. The systems and methods may, for example, be used in conjunction with a robotic surgical system.

Generally, in some embodiments, an apparatus includes a base, a member, and at least one tracking element. The base can be configured to couple to a surface of a patient at a preliminary port location for a robotic arm (e.g., via suction or an adhesive material). The member can be coupled to the base and can include a first end and a second end opposite the first end. The at least one tracking element can be coupled to the member and can be configured to allow tracking of the member relative to the preliminary port location.

In some embodiments, the member may be coupled to the base via a flexible joint. For example, the flexible joint may be configured such that the member is pivotable relative to the base. In some variations, the member may be rotationally fixed relative to the base.

At least one tracking element may be disposed at the second end of the member, to track movement of the second end of the member relative to the preliminary port location. The tracking element may, for example, include an infrared reflective material, an electromagnetic transmitter, or any suitable tracking marker or other tracking technology. Furthermore, in some variations, one or more tracking elements may be arranged in a pattern on the member (e.g., a two-dimensional pattern or three-dimensional pattern).

In some embodiments, the apparatus may further include a marking element configured to mark the preliminary port location on the patient (e.g., to identify the location as a suitable port location for a robotic surgical system). For example, the base and/or the member may define a lumen such that a marking element may be inserted through the lumen. When the base is disposed on the patient, the marking element may be inserted through the lumen and placed into marking contact with the surface of the patient. In some embodiments, a marking element may be engaged with a member that is transitionable between an extended configuration and a compressed configuration. When the base is coupled to the patient, the marking element may be spaced apart from the patient when the member is in the extended configuration, and may be in contact with the patient when the member is in the compressed configuration.

Generally, in some embodiments, a method includes receiving the location of at least one tracking element associated with a port placement guide positioned at a preliminary port location on a surface of a patient. A workspace may be analyzed around the preliminary port location based at least in part on the received location of the at least one tracking element. A port location may be associated with the preliminary port location based at least in part on the analysis of the workspace around the preliminary port location. A distal end of a robotic arm may be registered to the port location, and the distal end of the robotic arm may be manipulated toward the port location. Manipulating the distal end of the robotic arm toward the port location may, for example, be at least in part automatically performed (e.g., via a trajectory following algorithm) and/or assistively driven in combination with manual manipulation (e.g., via one or more virtual fixtures).

In some embodiments, analyzing the workspace around the preliminary port location may, for example, include assessing the preliminary port location relative to an anatomical feature of the patient and/or an access location associated with an intended procedure (e.g., an access location based on a template associated with an intended surgical procedure). As another example, analyzing the workspace may include assessing the location of a second robotic arm, a location of a second preliminary port location, and/or a location of an actual port location (e.g., a second port location already selected for use in a surgical procedure). In some embodiments, the method may include receiving a second location associated with the port placement guide positioned a second preliminary port location on the patient. For example, in these embodiments, analysis of the workspace may be repeated for different preliminary port locations of the port placement guide, before associating a suitable preliminary port location with an actual port location for use during a surgical procedure.

Generally, in some embodiments, a method of using a port placement guide may include positioning a port placement guide at a preliminary port location on a surface of a patient, and identifying a port location for a robotic arm based on an analysis of a workspace around the preliminary port location. In some embodiments, the method may include repositioning the port placement guide to different preliminary port locations (e.g., to a second preliminary port location). The identified port location may be marked with a marking element. After identifying a port location for the robotic arm, the port placement guide may be removed from the preliminary port location, and the robotic arm may be moved toward the port location. Furthermore, the method may further include creating an incision at the identified port location, at least partially inserting a medical instrument (e.g., cannula) through the port location, and coupling the distal end of the robotic arm to the medical instrument.

BRIEF DESCRIPTION OF THE DRAWINGS

FIG. 10 is a perspective view illustration of a port placement guide, according to an embodiment.

FIGS. 17A-17E illustrate a method of using a port placement guide to identify one or more port locations, according to an embodiment.

DETAILED DESCRIPTION

Non-limiting examples of various aspects and variations of the invention are described herein and illustrated in the accompanying drawings.

Systems and methods for guiding port placement on a patient and maneuvering a robotic arm toward the port location are described herein. The systems and methods may, for example, be used in conjunction with a robotic surgical system. In some embodiments, an apparatus includes a base, a member, and at least one tracking element. The base can be configured to couple to a patient (e.g., a surface of a patient) at a preliminary port location for a robotic arm. The member can be coupled to the base and can comprise a first end and a second end opposite the first end. The at least one tracking element can be coupled to the member and can be configured to allow tracking of the member relative to the preliminary port location.

In some embodiments, a method includes receiving the location of at least one tracking element associated with a port placement guide positioned at a preliminary port location on a surface of a patient. A workspace can be analyzed around the preliminary port location based at least in part on the received location of the at least one tracking element. A port location can be associated with the preliminary port location based at least in part on the analysis of the workspace around the preliminary port location. A distal end of a robotic arm can be registered to the port location. The distal end of the robotic arm can be manipulated toward the port location.

In some embodiments, a method of using a port placement guide includes positioning a port placement guide at a preliminary port location on a surface of a patient. The port placement guide can, for example, include a base, a member, and at least one tracking element. A port location for a robotic arm can be identified based at least in part on an analysis of a workspace around the preliminary port location. The port placement guide can be removed from the preliminary port location. The robotic arm can be moved toward the port location.

Surgical Procedure Overview

Figure 1:
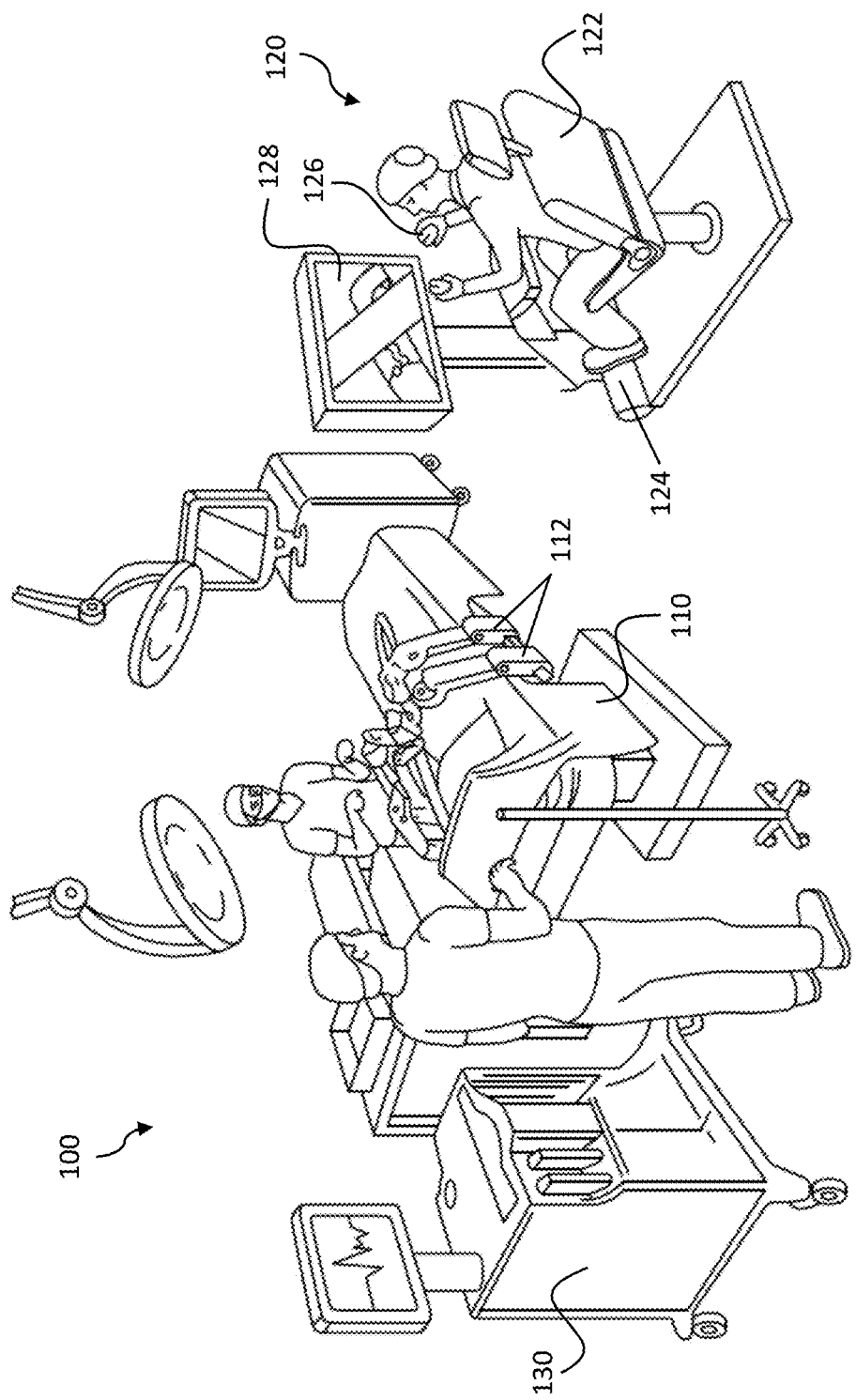
FIG. 1 is an overview schematic of an exemplary operating room arrangement with a robotic surgical system.

FIG. 1 is an illustration of an exemplary operating room environment with a robotic surgical system 100. As shown in FIG. 1, the robotic surgical system 100 comprises a user console 120, a control tower 130, and one or more robotic arms 112 located at a robotic platform 110 (e.g., table, bed, etc.), where surgical instruments (e.g., with end effectors) are attached to the distal ends of the robotic arms 112 for executing a surgical procedure. The robotic arms 112 are shown as a table-mounted system, but in other configurations, the robotic arms may be mounted to a cart, ceiling or sidewall, or other suitable support surface.

Generally, a user, such as a surgeon or other operator, may use the user console 120 to remotely manipulate the robotic arms 112 and/or surgical instruments (e.g., in tele-operation). The user console 120 may be located in the same operating room as the robotic system 100, as shown in FIG. 1. In other environments, the user console 120 may be located in an adjacent or nearby room, or tele-operated from a remote location in a different building, city, or country, etc. The user console 120 may comprise a seat 122, foot-operated controls 124, one or more handheld user interface devices 126, and at least one user display 128 configured to display, for example, a view of the surgical site inside a patient (e.g., captured with an endoscopic camera). As shown in the exemplary user console 120, a user located in the seat 122 and viewing the user display 128 may manipulate the foot-operated controls 124 and/or handheld user interface devices 126 to remotely control the robotic arms 112 and/or surgical instruments mounted to the distal ends of the arms.

In some variations, a user may operate the surgical robotic system 100 in an "over the bed" (OTB) mode, in which the user is at the patient's side and simultaneously manipulating a robotically-driven instrument/end effector attached thereto (e.g., with a handheld user interface device 126 held in one hand) and a manual laparoscopic tool. For example, the user's left hand may be manipulating a handheld user interface device 126 to control a robotic surgical component, while the user's right hand may be manipulating a manual laparoscopic tool. Accordingly, in these variations, the user may perform both robotic-assisted MIS and manual laparoscopic surgery on a patient.

During an exemplary procedure or surgery, the patient may be prepped and draped in a sterile fashion, and anesthesia may be achieved. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 124, user interface devices 126, and/or other suitable controls to manipulate various end effectors and/or imaging systems to perform the surgery. Manual assistance may be provided at the procedure table by other personnel, who may perform tasks including but not limited to retracting tissues, or performing manual repositioning or tool exchange involving one or more robotic arms 112. Other personnel may be present to assist the user at the user console 120. When the procedure or surgery is completed, the robotic system 100 and/or user console 120 may be configured or set in a state to facilitate one or more post-operative procedures, including but not limited to robotic system 100 cleaning and/or sterilization, and/or healthcare record entry or printout, whether electronic or hard copy, such as via the user console 120.

In some variations, the communication between the robotic platform 110 and the user console 120 may be through the control tower 130, which may translate user commands from the user console 120 to robotic control commands and transmit them to the robotic platform 110. The control tower 130 may transmit status and feedback from the robotic platform 110 back to the user console 120. The connections between the robotic platform 110, the user console 120, and the control tower 130 may be via wired and/or wireless connections, and may be proprietary and/or performed using any of a variety of data communication protocols. Any wired connections may be built into the floor and/or walls or ceiling of the operating room. The robotic surgical system 100 may provide video output to one or more displays, including displays within the operating room as well as remote displays accessible via the Internet or other networks. The video output or feed may be encrypted to ensure privacy, and all or one or more portions of the video output may be saved to a server, an electronic healthcare record system, or other suitable storage medium.

Robotic Arm and Surgical Tool Overview

Figure 2A:
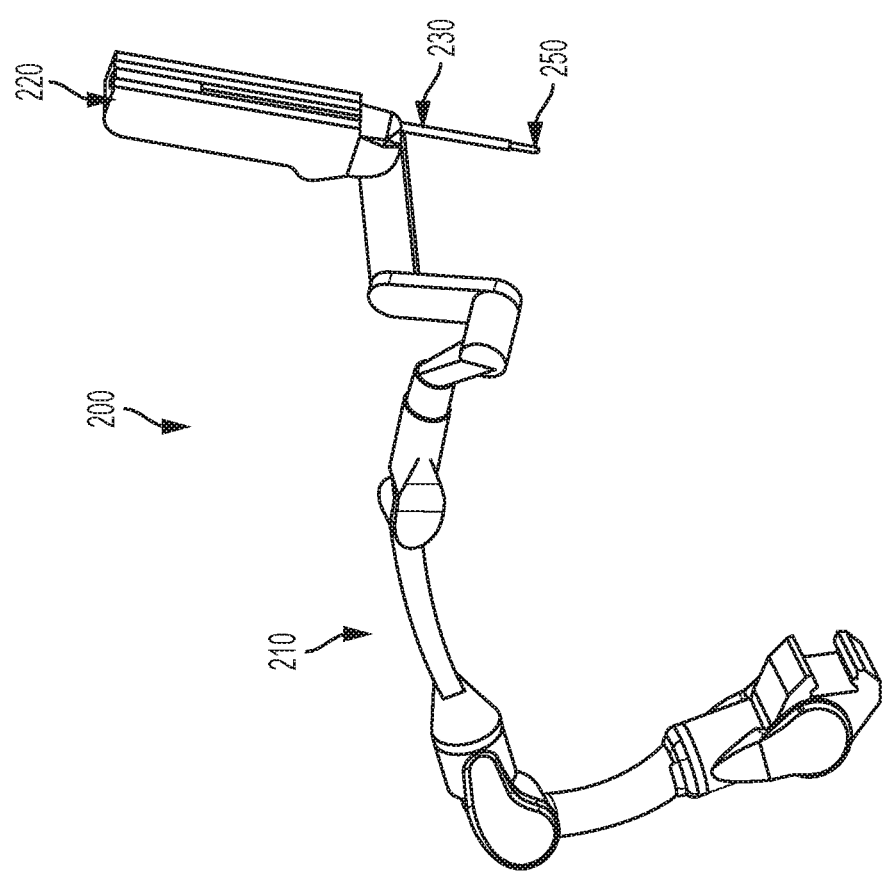
FIG. 2A is a schematic illustration of one exemplary variation of a robotic arm manipulator, tool driver, and cannula with a surgical tool.

Generally, a robotic or robotic-assisted surgical system (e.g., to enable a minimally-invasive surgical procedure) may include one or more robotic arms for manipulating surgical tools, such as during minimally-invasive surgery. For example, as shown in the exemplary schematic of FIG. 2A, a robotic assembly 200 may include a robotic arm 210 and a tool driver 220 generally attached to a distal end of the robotic arm 210. A cannula 230 coupled to the end of the tool driver 220 may receive and guide a surgical tool 250. Furthermore, the robotic arm 210 may include a plurality of links that are actuated so as to position and orient the tool driver 220.

For use in a surgical procedure, at least one robotic arm 210 may be mounted to an operating table on which a patient lies (or may be mounted to a cart, ceiling, sidewall, etc. near the patient). To create a port for enabling introduction of a surgical tool into the patient, a cannula assembly (e.g., a cannula 230 and obturator) may be at least partially inserted into the patient through an incision or entry point in the patient (e.g., in an abdominal wall). The cannula 230 may be coupled to a distal end of the tool driver 220 (as depicted in FIG. 1A) during such cannula placement in the patient (or in some variations, after placement). After the cannula is placed, the obturator may be removed, and the links in the robotic arm 210 may be controlled to maneuver the tool driver 220.

Figure 2C:
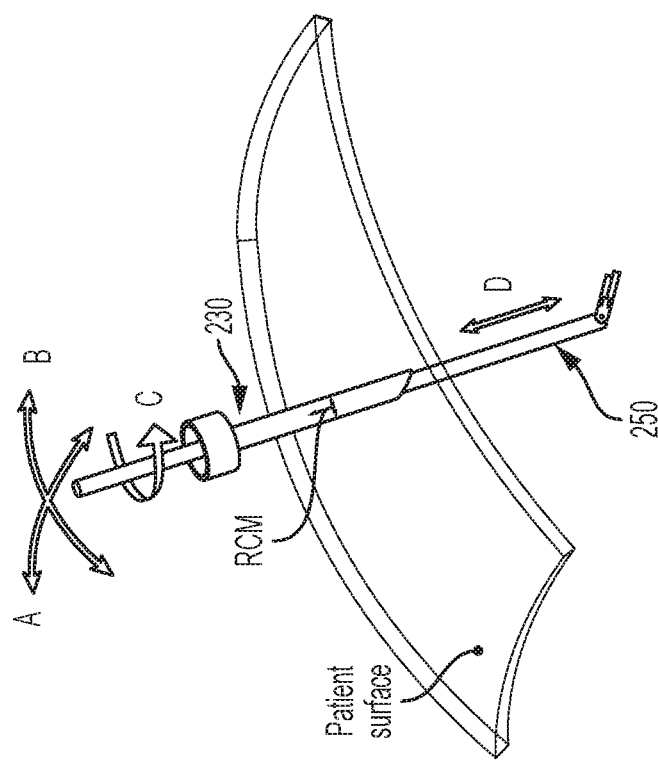
FIG. 2C is a schematic illustration of one exemplary variation of a cannula and surgical tool and their degrees of freedom of movement.
Figure 2B:
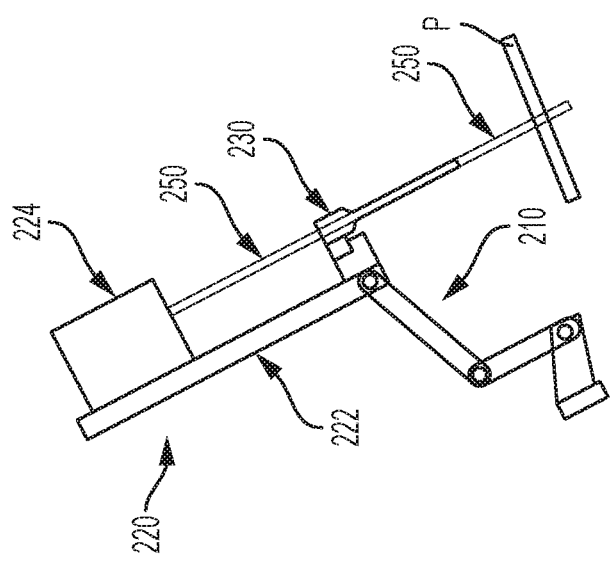
FIG. 2B is a schematic illustration of one exemplary variation of a tool driver and a cannula with a surgical tool.

A proximal portion of the surgical tool 250 may be coupled to the tool driver 220 such that, as shown in FIG. 2B, at least a portion (e.g., tool shaft) passes through the cannula and into the patient P. For example, a proximal portion of the surgical tool 250 may be coupled to a carriage 224 that is movable along a stage 222, and the stage 222 may be coupled to a distal end of the robotic arm 210 for positioning of the tool driver 220.

When a surgical tool 250 is coupled to the tool driver 220, actuation of the robotic arm 210 and/or the tool driver 220 may provide for one or more various degrees of freedom of the tool as shown in FIG. 2C, including but not limited to movement in a yaw direction or spherical roll (arrow A), movement with the cannula in a pitch direction (arrow B), tool rotation (arrow C) axially within the cannula 130, and/or tool translation (arrow D) within the cannula 130. For example, movement in the yaw and/or pitch directions may be controlled through actuation of at least a portion of the robotic arm 210. Tool movement in the yaw and/or pitch directions may, in some variations, be constrained to movement around a center of spherical rotation, or mechanical remote center of motion (RCM). Furthermore, tool rotation axially within the cannula 230 may be controlled through one or more tool driver actuators in the carriage 224 coupled to the surgical tool 250 (directly or indirectly through a sterile barrier, etc.), and tool translation within the cannula 230 may be controlled through one or more tool driver actuators that cause the carriage 224 to translate along the stage 222.

A distal portion of the surgical tool 250 may include an end effector, and actuators in the carriage 224 may be further controlled to actuate the tool 250 to perform various tasks during the surgical procedure (e.g., cutting, grasping, etc.) in accordance with the particular kind of end effector. Additionally, the tool 250 may be withdrawn from the port and decoupled from the tool drive 220 to exchange with another tool, such as another tool having an end effector with different functionality.

Port Placement Guide

As further described below, in some embodiments, a port placement guide can be used to assist a user (e.g., surgical staff or a surgeon) in identifying suitable or preferred port placement on the surface of a patient. Selection of a suitable or preferred port placement may, for example, be based at least in part on increasing access to a surgical worksite, locating an RCM of a cannula relative to a port location that reduces risk of injury to the patient at reduced risk of leaks at the cannula-patient interface, avoiding collisions between objects such as robotic arms, etc. Furthermore, in some embodiments, the port placement guide can provide information about a port location to assist docking of a robotic arm at the port location (e.g., moving the robotic arm toward a cannula or other device at the port location). The port placement guide can, for example, reduce surgical procedure setup time by expediting the port location selection process, reducing the risk of issues such as arm collisions or failed cannula docking attempts. Furthermore, in some embodiments, the port placement guide can help with training users for robotic surgery, can help improve consistency in port placement between different surgical procedures, and the like.

Figure 3:
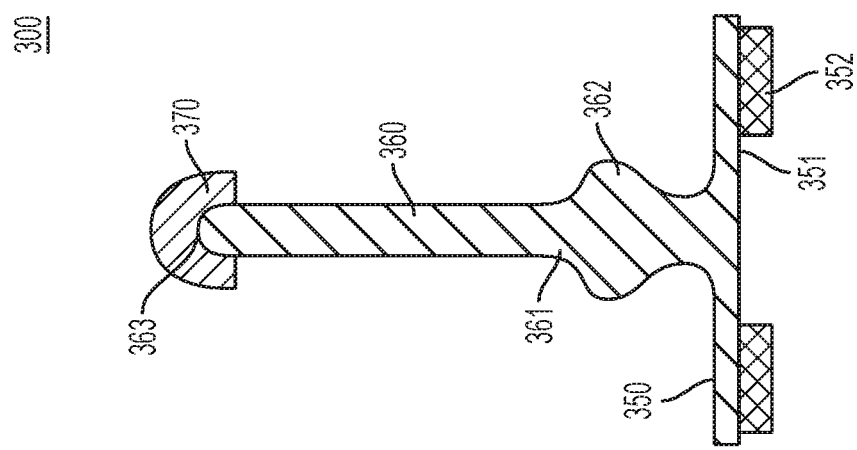
FIG. 3 is a cross-sectional illustration of a port placement guide, according to an embodiment.

Generally, in some variations, as shown in FIG. 3, a port placement guide 300 may include a base 350 configured to couple to a surface of a patient at a preliminary port location for a robotic arm, a member 360 coupled to the base, and at least one tracking element 370 coupled to the member. A first end 361 of the member 360 can be coupled to the base 350 via a flexible joint 362. A second end 363 of the member 360 can be coupled to the tracking element 370. The port placement guide 300 can be coupled to a surface (e.g., the skin) of a patient in a location where the user intends to place or is considering placing a port in the surface (e.g., a robotic or laparoscopic port).

The base functions to couple the port placement guide to the patient. The base 350 can include a securement element 352 such that the base 350 can be attached to the surface of the patient via the securement element 352. The securement element 352 can include an adhesive material (e.g., a temporary glue or adhesive) such that the base 350 can be attached to the surface of the patient via the adhesive material. In some embodiments, the securement element 352 can include a double-sided bonding strip or foam. In some embodiments, the securement element 352 can include and/or be shaped as a disc-shaped (e.g., donut-shaped) pad.

The pad can include any suitable material, such as rubber, plastic, and/or metal. The pad can also include or be coated with an adhesive material such that the pad can be attached to the surface of the patient.

In some embodiments, although not shown, the securement element 352 can be formed as or include one or more suction cups. The base 350 can adhere to the surface of the patient via pressure applied to the one or more suction cups by the base 350. The one or more suction cups can be formed of any suitable material, such as, for example, rubber. In some embodiments, a medium such as saline or gel can be applied to the patient-facing surface of the one or more suction cups and/or to the surface of the patient to aid in sealing the one or more suction cups to the surface of the patient. In some embodiments, an adhesive material can be disposed on the patient-facing surface of the one or more suction cups to improve the securement of the base 350 to the surface of the patient.

After attachment, the securement element 352 can be removable from the surface of the patient. In some embodiments, the securement element 352 can be reattachable to the patient such that the guide 300 can be moved between a first location and a second location on the patient. In some embodiments, the securement element 352 can be affixed to a patient-facing side 351 of the base 350 prior to coupling the guide 300 to the surface of the patient. In some embodiments, the securement element 352 can be coupled to the surface of the patient prior to the base 350 of the guide 300 being attached to the securement element 352.

In some embodiments, the member 360 can be generally centered on the base 350. For example, as shown in FIG. 3, the member 360 can be coaxially aligned with a central axis of the base 350 such that the member 360 extends substantially normal to the base 350 when not under the influence of any external forces (i.e., not being pivoted relative to the base 350 by a user). Alternatively, the member 360 may extend from the base 350 at any suitable angle. Furthermore, in some embodiments, the member 360 can be off-center relative to the base 350 (e.g., the first end of the member 360 can be laterally offset from the central axis of the base 350). Although the member 360 is shown as being elongated, the member 360 can be formed in any suitable shape.

The flexible joint 362 can allow the member 360 (or a portion of the member 360) to pivot relative to the base 350. Said another way, in some embodiments, the member 360 can rotate relative to the base 350 in any direction relative to a plane including the patient-facing side 351 of the base 350. For example, the flexible joint 362 can allow the member 360 to pivot relative to the surface of the patient, such that when the guide 300 is coupled to the surface of the patient, the member 360 can move similarly to a medical instrument (e.g., a cannula) installed in a port at the location of the guide 300 on the surface of the patient. In some embodiments, the flexible joint 362 can be disposed at the interface between the member 360 and the base 350. In some embodiments, the flexible joint 362 can be disposed along the member 360 such that an upper portion of the member 360 (e.g., a portion on a first side of the flexible joint 362) can pivot relative to a lower portion of the member 360 (e.g., a portion on a second side of the flexible joint 362).

In some embodiments, the base 350, the flexible joint 362, and the member 360 can be formed as a one-piece, integral structure. The base 350 and the member 360 can be formed of a more rigid material than the flexible joint 362, which can be relatively more elastic. Alternatively, in some embodiments, the flexible joint 362 can be formed as a different structure and can be coupled between the base 350 and the member 360 during assembly. For example, the flexible joint 362 can include a flexible bellows or a ball and socket coupling such that the member 360 can pivot relative to the base.

The tracking element 370 can be any suitable type of tracking element and formed in any suitable shape such that the location and/or orientation of the tracking element 370 in a three dimensional space can be detected and observed. For example, in some embodiments, the tracking element 370 can include infrared reflective material such that the location of the tracking element 370 can be detected by an external optical infrared tracking system (not shown). In some embodiments, the tracking element 370 can include an electromagnetic sensor and/or an electromagnetic transmitter such that the position (e.g., X, Y, and/or Z coordinates within a space) and the orientation (e.g., yaw, pitch, and/or roll) of the tracking element 370 can be monitored by an electromagnetic-based tracking system (not shown). For example, the tracking element 370 can include a transmitter that emits an electromagnetic dipole field which can be evaluated to determine the position and/or orientation of the tracking element 370. In some embodiments, rather than including a single tracking element 370 as shown in FIG. 3, the guide 300 can include multiple tracking elements. For example, the guide 300 can include two, three, four, or more than four tracking elements. Various tracking elements that can be included in the guide 300 are shown and described in more detail below with respect to FIGS. 4-8.

As described above, the guide 300 can be coupled to the surface of the patient. The member 360 can then be pivoted relative to the base 350 and the patient over any suitable range in any suitable direction (e.g., through the range of motion of the flexible joint 362). A tracking system (not shown) can be used to detect the position and/or orientation of the tracking element 370 and to determine the location of the guide 300 on the surface of the patient. For example, the tracking system can use the locations of the tracking element 370 at various pivot angles relative to the base 350 to identify the location of the guide 300. The tracking system can then associate the guide 300 with a potential port location. In some embodiments, a point cloud can be generated as the member 360 moves the tracking element 370 through a range of motion of the flexible joint 362 in various directions. The point cloud can then be used to infer the location of the flexible joint 362 and/or the base 350. The guide 300 can then be removed from the surface of the patient and an incision can be made in the surface of the patient at the potential port location to create a port.

Although the guide 300 is shown as including the flexible joint 362 and the member 360 is described as being pivotable relative to the base 350, in some embodiments, the member 360 can be rotationally fixed relative to the base 350. In other words, the member 360 can be substantially fixed relative to the base 350 (e.g., the interface between the member 360 and the base 350 can be substantially rigid). In such embodiments, the location and/or orientation of the tracking element 370 can be detected such that the tracking system can use the location and/or orientation to identify the location of the guide 300 relative to a patient.

Figure 5:
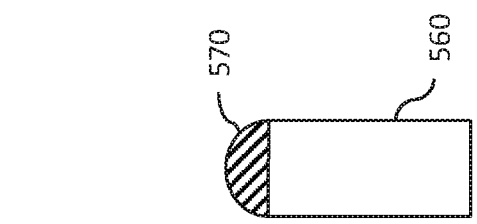
FIG. 5 is a perspective view illustration of a portion of a member coupled to a tracking element, according to an embodiment.
Figure 4:
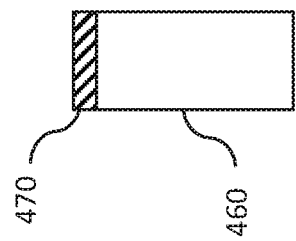
FIG. 4 is a perspective view illustration of a portion of a member coupled to a tracking element, according to an embodiment.

In some embodiments, the base 350, member 360, and/or other suitable portion of the guide 300 can be configured to function as an artificial body wall and/or provide additional structural support during a surgical procedure. For example, during some procedures, a sufficient body wall or patient surface may be absent from a surgical site (e.g., a procedure involving a natural orifice, or a procedure in which a large incision has been made, etc.), such that it is difficult to place a cannula and/or obtain a proper seal between the cannula and the patient tissue at that surgical site. In some embodiments, the port placement guide may be shaped and/or sized to supplement the surgical site. For example, the base, member, and/or other suitable portion of the guide 300 may be sufficiently large (e.g., in height and/or diameter) to receive a cannula when the guide 300 is coupled to a surface to a patient. Furthermore, in some embodiments, the guide 300 may sealingly engage the cannula during a surgical procedure, similar to a patient body wall. FIGS. 4-8 illustrate examples of various tracking elements and tracking assemblies that can be included in a port placement guide, such as the guide 300 or any of the other guides described herein. FIG. 4 is an illustration of a portion of a member 460 coupled to a tracking element 470. The member 460 can be the same or similar in structure and/or function to any of the member described herein, such as the member 360. As shown, the tracking element 470 can be shaped as a flat disc. The tracking element 470 can, for example, be formed of or include infrared reflective material such that the location of the tracking element 470 can be detected by an optical infrared tracking system (not shown). FIG. 5 is an illustration of a portion of a member 560 coupled to a tracking element 570. The member 560 can be the same or similar in structure and/or function to any of the member described herein, such as the member 360. The tracking element 570 can be formed as a hemisphere or such that the tracking element 570 has a rounded upper surface. Similar to the tracking element 470, the tracking element 570 can be formed of or include infrared reflective material such that the location of the tracking element 570 can be detected by an optical infrared tracking system (not shown). The tracking element 570, however, may have any suitable shape.

Figure 6:
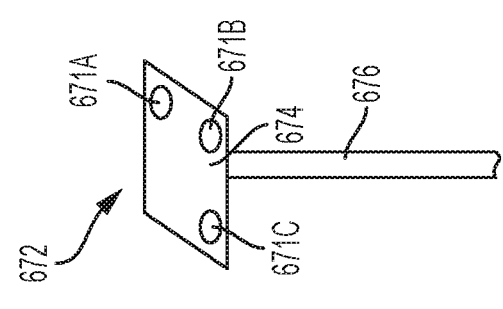
FIG. 6 is a perspective view illustration of a tracking assembly, according to an embodiment.

Although FIGS. 4 and 5 show only one tracking element coupled to a member, in some embodiments an array of multiple tracking elements can be disposed on or near a second end of a member, such as the member 360 or any of the members described herein. An array of tracking elements can be used to provide location and/or orientation information to a tracking system. For example, FIG. 6 is an illustration of an exemplary tracking assembly 672. The tracking assembly 672 can include a plate 674 having a two dimensional surface. Alternatively, in some variations, the plate 674 may include a three dimensional surface (e.g., a contoured surface). The plate 674 can be coupled to a second end of a member, such as any of the members described herein, via an extension member 676. In some embodiments, rather than being attached to a second end of a member via the extension member 676, the plate 674 can be coupled directly to the second end of the member. As shown in FIG. 6, an array of tracking elements 671A-C is disposed on the two dimensional surface of the plate 674. Each of the tracking elements 671A-C can be formed of or include infrared reflective material such that the location of each of the tracking elements 671A-C can be detected by an optical infrared tracking system. Although three tracking elements are shown on the plate 674, any suitable number of tracking elements can be disposed on the plate 674.

Figure 7:
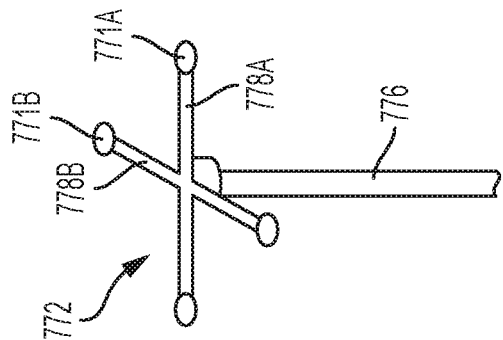
FIG. 7 is a perspective view illustration of a tracking assembly, according to an embodiment.

FIG. 7 is an illustration of a tracking assembly 772. The tracking assembly 772 can include an array of tracking elements 771 (e.g., tracking element 771A and tracking element 771B) coupled to one another via supporting members 778 (e.g., supporting member 778A and supporting member 778B). The tracking assembly 772 can also include an extension member 776 such that the supporting members 778 can be coupled to a second end of a member of a guide via the extension member 776, such as the member 360 of the guide 360 described above. Although the tracking assembly 772 shows an array of four tracking elements coupled to one another via four supporting members 778, the tracking assembly 772 can include any suitable number of tracking elements 771. Each supporting member 778 and tracking element 771 can be arranged at any suitable angle relative to the extension member 776 such that the tracking elements 771 are arranged as a three dimensional array. Each of the tracking elements 771 can be formed of or include infrared reflective material such that the location of each of the tracking elements 771 can be detected by an optical infrared tracking system.

Figure 8:
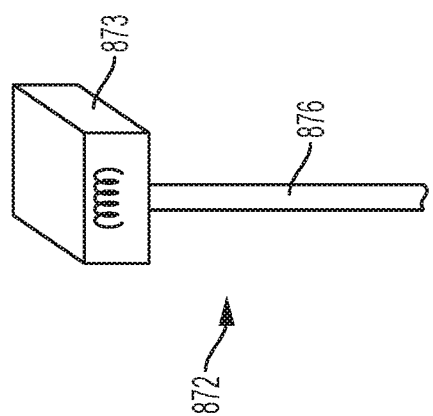
FIG. 8 is a perspective view illustration of a tracking assembly, according to an embodiment.

FIG. 8 is an illustration of a tracking assembly 872. The tracking assembly 872 can include an electromagnetic component 873. The electromagnetic component 873 can be coupled to a second end of a member of a guide, such as any of the members described herein, via an extension member 876. In some embodiments, rather than including the extension member 876, the electromagnetic component 873 can be coupled directly to the second member of the guide. The electromagnetic component 873 can include an electromagnetic sensor and/or an electromagnetic transmitter such that the position (e.g., X, Y, and/or Z coordinates within a space) and/or the orientation (e.g., yaw, pitch, and/or roll) of the tracking element 370 can be monitored by an electromagnetic-based tracking system (not shown). For example, the electromagnetic component 873 can include a transmitter that emits an electromagnetic dipole field which can be evaluated to determine the position and orientation of the electromagnetic component 873.

Figure 9C:
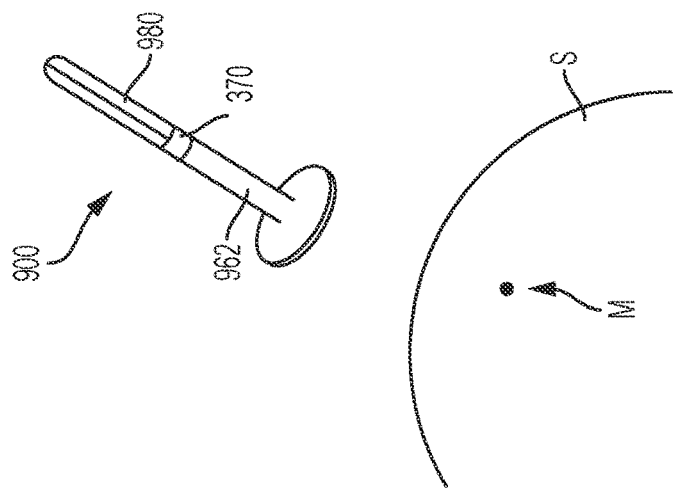
FIG. 9C is a perspective view illustration of the port placement guide of FIG. 9A in a third configuration relative to the surface of the patient.
Figure 9B:
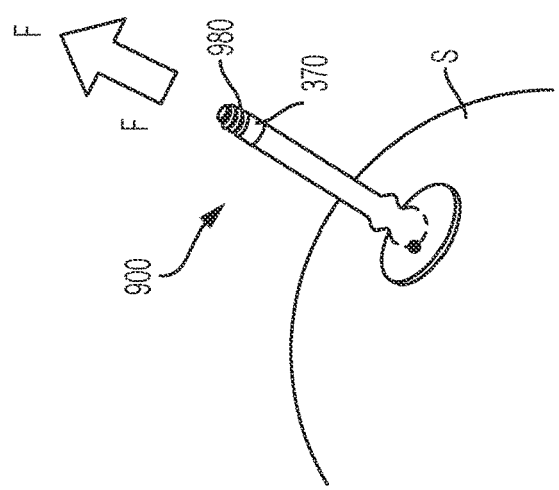
FIG. 9B is a perspective view illustration of the port placement guide of FIG. 9A in a second configuration relative to the surface of the patient.
Figure 9A:
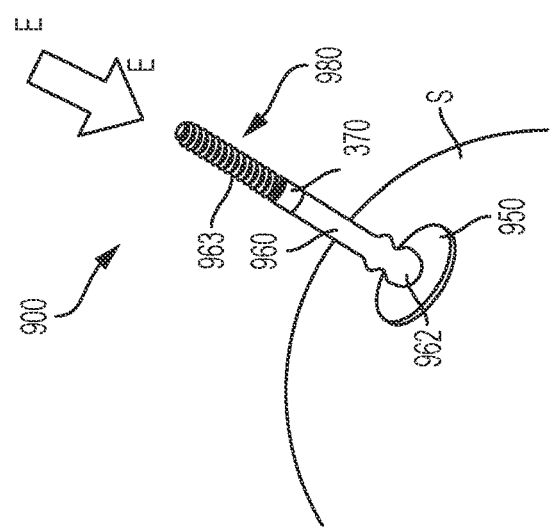
FIG. 9A is a perspective view illustration of a port placement guide in a first configuration relative to a surface of a patient, according to an embodiment.

In some embodiments, a port placement guide can include a marking element such that the port placement location on a surface of a patient can be marked (e.g., with ink or incision) and identified (e.g., after removal of the port placement guide). For example, as shown in FIGS. 9A-9C, a port placement guide 900 can include a marking element 980. The port placement guide 900 can include the same or similar structural and/or functional aspects to any of the port placement guides described herein, such as the port placement guide 300 described above with reference to FIG. 3. For example, the port placement guide 900 includes a base 950, a member 960, and a flexible joint 962 arranged such that the member 960 can pivot relative to the base 950. The port placement guide 900 can define a lumen (not shown) extending from an open proximal or second end 963 of the member 960 through the base 950. Said another way, the base 950, the member 960, and the flexible joint 962 can collectively define a lumen through which the marking element 980 can be translated. The marking element 980 can be formed and/or shaped as, for example, a pen or a marker, and can include a marking tip on a distal end of the marking element 980. In some embodiments, the marking element 980 can be coupled to the member 960 such that the marking element 980 is fixed to the member 960. The marking element 980 can be translated within and/or with the member 960 relative to the base 950 toward and away from a surface of a patient. In some embodiments, the marking element 980 may include an adhesive element (e.g., adhesive pad or other suitable marker) that is configured to couple to the surface of the patient to mark the port placement location. Additionally or alternatively, the marking element 980 may include a scalpel or other tool to make a small incision at the port placement location.

In use, as shown in FIG. 9A, for example, the guide 900, comprising member 960 and tracking element 370 coupled to the member 960, can be placed on a surface S of a patient at an intended port placement location. The marking element 980 can then be translated in the direction of arrow E-E toward the surface S of the patient. As shown in FIG. 9B, when the marking element 980 has been translated or pushed in the direction of arrow E-E such that the marking tip of the marking element 980 is in marking contact with the surface S, the marking element 980 can be partially disposed within the member 960. After marking the surface S, the entire guide 900 can be moved in the direction of arrow F-F in FIG. 9B such that the guide 900 can be removed from the surface S of the patient, leaving mark M behind on the surface as shown in FIG. 9C. As also shown in FIG. 9C, the marking element 980 can be extended relative to the base 950 such that the flexible joint 562 is stretched or extended, protecting the marking tip of the marking element 980 within the member 960. An incision can then be made at the location of mark M such that a port is created for insertion of a medical instrument (e.g., a cannula and/or a trocar).

In some embodiments, rather than being fixedly attached to a member or other portion of the port placement guide, a marking element can be separate from the guide and insertable through the guide. For example, as shown in FIG. 10, a port placement guide 1000 can include a marking element 1080 separable from the rest of the guide 1000. The port placement guide 1000 can include the same or similar structural and/or functional aspects as any of the port placement guides described herein. For example, the guide 1000 can include a base 1050 and a member 1060. The guide 1000 can also include a flexible joint 1062 such that the portion of the member 1060 above the flexible joint 1062 can pivot relative to the base 1050. The port placement guide 1000 can define a lumen 1064 extending from an open proximal or second end 1063 of the member 1060 through the base 1050. Said another way, the base 1050, the member 1060, and the flexible joint 1062 can collectively define a lumen through which the marking element 1080 can be inserted.

The marking element 1080 can be same or similar in structure and/or function to the marking element 980 described above with respect to FIG. 9. For example, the marking element 1080 can be formed and/or shaped as, for example, a pen or a marker (or include an adhesive marker), similar to that described above with reference to FIGS. 9A-9C. The marking element 1080 can include a marking tip 1082 on a distal end. Additionally, a tracking element 1070 can be disposed on a proximal end of the marking element 1080. The tracking element 1070 can include, for example, and of the tracking elements described herein such as the tracking elements shown and described with respect to FIGS. 5-8. The marking element 1080 can be shaped and sized such that the marking element 1080 can be disposed within the lumen 1064 defined by the guide 1000 and translated such that the marking tip 1082 is in marking contact with the surface of the patient.

More specifically, in some embodiments, the marking element 1080 can be inserted through the lumen 1064 of the guide 1000 and moved toward the surface of the patient relative to the member 1060 such that the marking element 1080 can mark the surface of the patient. In some embodiments, the member 1060 and/or the flexible joint 1062 can be axially compressible such that the marking element 1080 can be inserted into engagement with the member 1060 and can axially compress the guide 1000 toward the surface of the patient. Specifically, the marking element 1080 can engage with the member 1060 and the marking element 1080 and the member 1060 can collectively be pressed toward the surface of the patient such that the member 1060 and/or the flexible joint 1062 are compressed toward the surface of the patient and the marking tip 1082 can contact and mark the surface of the patient. The guide 1000 (or at least the marking element 1080) can then be removed from the surface of the patient and an incision can be made in the surface of the patient at the potential port location to create a port. In some embodiments, the guide 1000 can be removed and the port can be created at the location of the mark on the surface of the patient. In some embodiments, the marking element 1080 can be withdrawn from the lumen 1064 of the guide 1000, leaving the guide 1000 coupled to the surface of the patient. One or more medical instruments can then be inserted into the guide 1000 and into contact with the surface of the patient to create a port (e.g., make an incision) and/or perform a medical procedure through the guide 1000.

In some embodiments, when the marking element 1080 is inserted into the lumen 1064 of the guide 1000, the marking element 1080 can then be pivoted relative to the base 1050 by the user in various directions such that a tracking system can detect the location of the tracking element 1070. The tracking system can then use the location information to determine the location of the guide 1000, and, therefore, the location of the potential port.

In some embodiments, although not shown, the marking element 1080 can have a non-marking distal end rather than a marking tip. The marking element 1080 can then be inserted through the lumen 1064 and pivoted such that a tracking system can identify various locations of the tracking element 1070. The tracking system can then use the location information to identify the intended location of a port. In some embodiments, after being used for tracking, the marking element 1080 can be replaced within the guide 1000 with an instrument intended to mark and/or incise the surface of the skin. In some embodiments, as an alternative or in addition to the marking element 1080, the guide 1000 can include or receive a scalpel that can be inserted through the lumen 1064 to create a small incision at the potential port location, thus creating the port or a portion of a port. In some embodiments, alternatively or in addition to the marking element 1080, the guide 1000 can include a cannula that can be inserted through the lumen 1064 and through the surface of the patient, creating a port in the surface of the patient at the location of the guide 1000. In some embodiments, the guide 1000 can be removed from the surface of the patient, leaving the cannula disposed in the port.

Figure 11B:
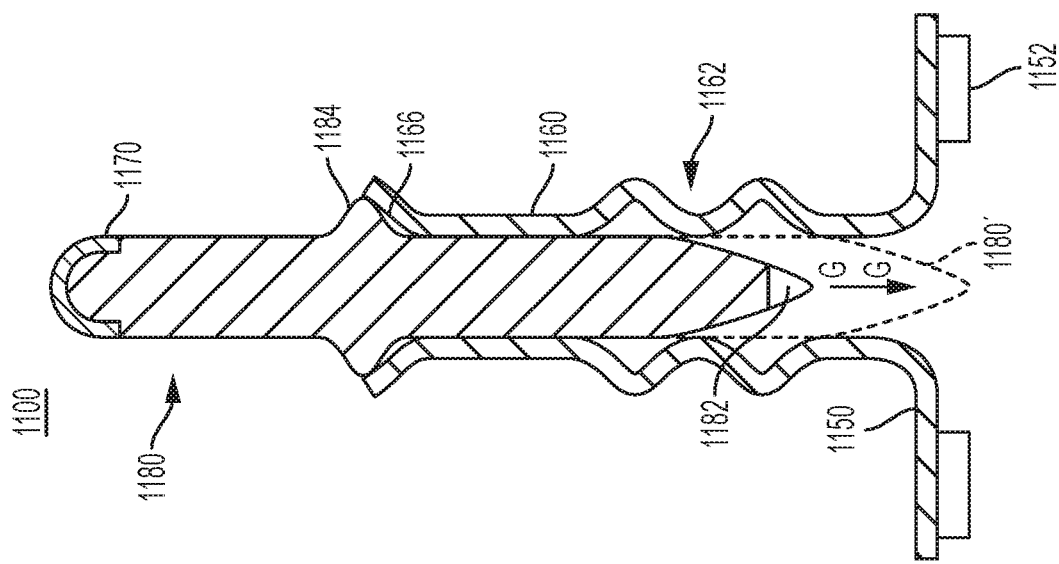
FIG. 11B is a cross-sectional illustration of a port placement guide including a marking element, according to an embodiment.
Figure 11A:
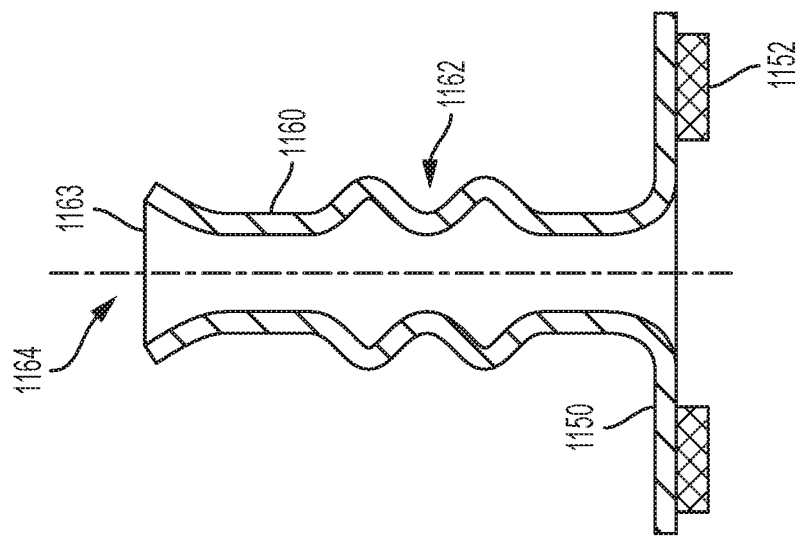
FIG. 11A is a cross-sectional illustration of part of a port placement guide, according to an embodiment.

In some embodiments, the marking element and the member may be configured to engage one another such that the marking element and at least a portion of the member move in tandem toward the surface of the patient. For example, in some embodiments, the marking element can include an engagement feature to axially engage the marking element with the member, such that movement of the marking element toward the surface of the patient also compresses the member toward the surface of the patient. For example, as shown in FIGS. 11A and 11B, a port placement guide 1100 can include a marking element 1180 with an engagement feature 1184. FIGS. 11A and 11B are cross-sectional illustrations of a port placement guide 1100 without a marking element, and a port placement guide 1100 with a marking element 1180, respectively. The port placement guide 1100 can include the same or similar structural and/or functional aspects as any of the port placement guides described herein. For example, the guide 1100 can include a base 1150, a member 1160, and a flexible joint 1162. The base 1150, the member 1160, and the flexible joint 1162 can be the same and/or similar in structure and/or function to the base 1050, the member 1060, and the flexible joint 1062, respectively. Additionally, the base 1150 includes a securement element 1152 which can be the same or similar in structure and/or function to any of the securement elements described herein, such as the securement element 352 described above with reference to FIG. 3. The guide 1100 can define a central lumen 1164 and can include a proximal end 1163.

As shown in FIG. 11B, the marking element 1180 can include a marking tip 1182 and a tracking element 1170. The marking element 1180 can be the same or similar in structure and/or function to any of the marking elements described herein, such as, for example, the marking element 1080 described with reference to FIG. 10. As described above, the marking element 1180 can also include the engagement feature 1184. The engagement feature 1184 can be in the form of a projection, flange, ring, or other suitable stop extending from the outer surface of the marking element 1180.

As shown in FIG. 11A, the guide 1100 can be disposed on a surface, such as a surface of a patient. As shown in FIG. 11B, the marking element 1180 can be inserted into the lumen 1164 of the guide 1100 such that the engagement feature 1184 can engage with the proximal end 1163 of the guide 1100. The marking element 1180 can then be moved in the direction of arrow G-G from the retracted position shown in FIG. 11B to a surface contacting position represented in phantom by 1180' such that the marking tip 1182 can contact and mark the surface of the patient. Due to the engagement between the engagement feature 1184 and the proximal end 1163 of the member 1160, the translation of the marking element 1180 in the direction of arrow G-G can compress the member 1160 and/or the flexible joint 1162 as the marking element 1180 approaches the surface of the patient. After marking the surface of the patient, the marking element 1180 can be removed and the guide 1100 can remain on the surface of the skin. One or more medical instruments can then be inserted into the guide 1100 and into contact with the surface of the patient to create a port (e.g., make an incision) and/or perform a medical procedure through the guide 1100. Alternatively, the guide 1100 can be removed prior to the creation of the port, which can be created in the surface at the location of the mark created by the marking element 1180.

Figure 12:
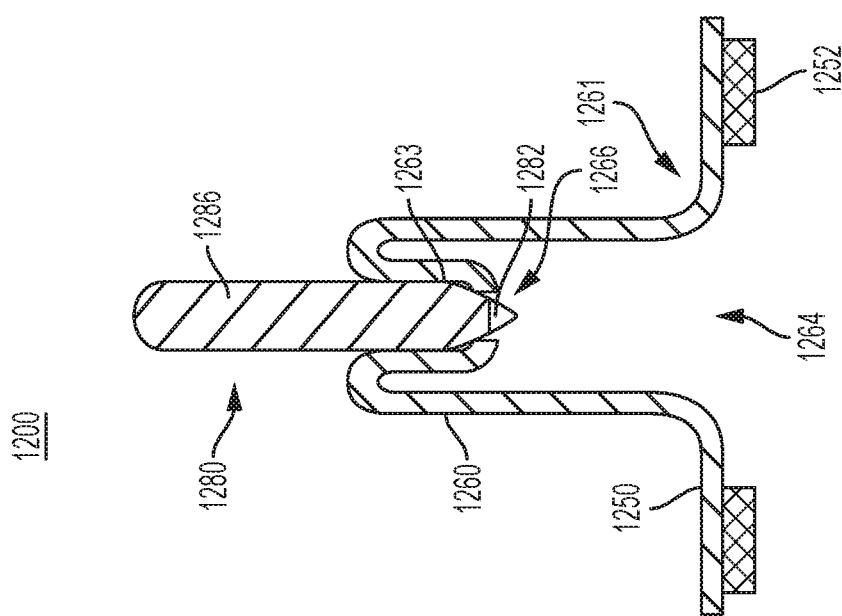
FIG. 12 is a cross-sectional illustration of a port placement guide, according to an embodiment.

FIG. 12 illustrates another example of the marking element and at least a portion of the member moving in tandem. FIG. 12 is a cross-sectional illustration of a port placement guide 1200. Aspects of the port placement guide 1200 can be the same or similar in structure and/or function to that of any of the port placement guides described herein. For example, the guide 1200 can include a marking element 1280. The guide 1200 can include a base 1250 and a member 1260. The base 1250 can include a securement element 1252, which can be the same or similar to any of the securement elements described herein, such as the securement element 352. The member 1260 can include a first end 1261 and a second end 1263, the second end 1263 defining an opening 1266 to a lumen 1264. The marking element 1280 can be the same or similar in structure and/or function to any of the marking elements described herein. For example, the marking element 1280 can include a marking tip 1282. The opening 1266 of the second end 1263 of the member 1260 can have a diameter large enough to receive the marking tip 1282 of the marking element 1280 but smaller than the diameter of the body 1286 of the marking element 1280.

As shown in FIG. 12, the member 1260 can have an inverted proximal end or be manipulated such that the second end 1263 is inverted such that the second end 1263 of the member 1260 is folded into the lumen 1264. The marking element 1280 can engage the second end 1263 of the member 1260 such that movement of the marking element 1280 toward the surface of the patient folds the member 1260 toward a surface of a patient. The marking element 1280 can then be moved distally into marking contact with a surface of a patient, translating the second end 1263 of the member 1260 toward the first end 1261 of the member as the marking element 1280 moves toward the base 1250 and eventually to the surface of the patient.

Figure 13B:
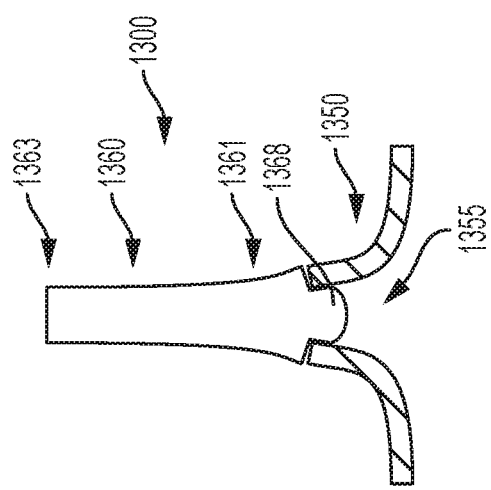
FIGS. 13A and 13B are cross-sectional illustrations of a base and a port placement guide including the base, respectively, according to an embodiment.
Figure 13A:
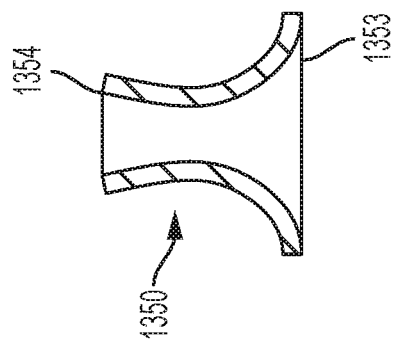

FIGS. 13A and 13B are cross-sectional illustrations of a base 1350 of a port placement guide, and a port placement guide 1300 including the base 1350, respectively. The guide 1300 can be attached to a surface of a patient using suction, for example. The base 1350 can have a first end 1353 and a second end 1354, and can define a lumen extending through the base 1350 from the first end 1353 to the second end 1354. As shown in FIG. 13B, the guide 1300 can include a member 1360. The member 1360 can have a first end 1361 and a second end 1363. The member 1360 can include an engagement feature 1368 projecting from the first end 1361. The engagement feature 1368 can be shaped and sized such that the engagement feature 1368 can couple to (e.g., sealingly engage with) the second end 1354 of the base 1350.

In use, the base 1350 can be placed on a surface of a patient. The member 1360 can be engaged with the base 1350 to define an interior cavity 1355 by engaging the engagement feature 1368 of the first end 1361 of the member 1360 with the second end 1354 of the base 1350. The member 1360 can then be pressed toward the surface of the patient such that gaseous fluid (e.g., air) is pushed out of the interior cavity 1355 and a seal is created between the base 1350, the member 1360, and the surface of the patient due to the suction of the base 1350 and the member 1360 on the surface of the patient.

Figure 14:
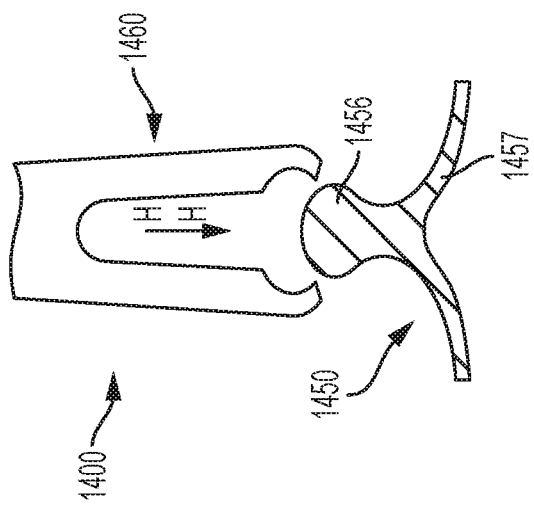
FIG. 14 is a cross-sectional illustration of a port placement guide, according to an embodiment.

FIG. 14 is a cross-sectional illustration of a port placement guide 1400. The guide 1400 includes a base 1450 and a member 1460. The base 1450 includes an engagement feature 1456 and a patient-facing surface 1457. As can be seen in FIG. 14, the patient-facing surface 1457 can be shaped such that the base 1450 can be coupled to a surface of a patient via suction. For example, the base 1450 can be disposed on a surface of a patient in an intended location and pressed toward the surface to create a seal between the surface and the base 1450. The member 1460, having a complementary engagement recess 1469 to the engagement feature 1456 of the base 1450, can be translated in the direction of arrow H-H and engaged with the base 1450.

Figure 15:
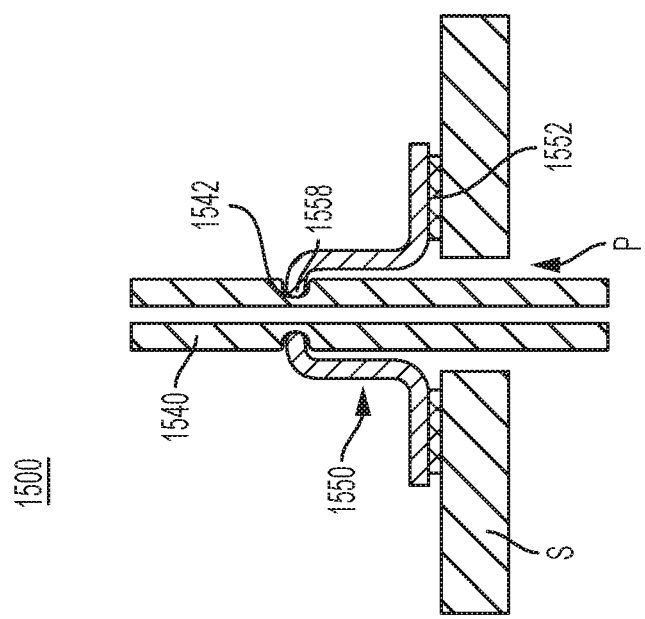
FIG. 15 is a cross-sectional illustration of a port placement guide, according to an embodiment.

FIG. 15 is a cross-sectional illustration of a port placement guide 1500. The guide 1500 includes a base 1550. The base 1550 can be the same or similar in structure and/or function to any of the bases described herein. For example, the base 1550 can include a securement element 1552, which can be the same or similar to any of the securement elements described herein, such as the securement element 352. The base 1550 can also include an engagement feature 1558. The engagement feature 1558 can be any suitable shape, such as a flange or a plurality of prongs. In some embodiments, the base engagement feature 1558 can provide a seal around a medical tool or instrument inserted through the base 1550 such that fluids are prevented from leaking from a port P.

The base 1550 can be disposed on a surface S of a patient in a location where a port P is intended to be created. In some embodiments, a marking element (not shown) including a tracking element can be engaged with the base 1550 to assist a tracking system in identifying the location of the port prior to the creation of the incision. Once the port P is created in the surface S, as shown in FIG. 15, an instrument 1540 (e.g., a cannula) can be inserted through the base 1550 and through the port P. The instrument 1540 can define a recess 1542 corresponding to the engagement feature 1558 of the base 1550 such that the insertion depth of the instrument 1540 is limited. For example, the instrument 1540 can be slid through the base 1550, and the engagement feature 1558 can apply pressure to the outer surface of the instrument 1540. When the recess 1542 of the instrument 1540 reaches the engagement feature 1558, the engagement feature 1558 can engage with the recess 1542 such that the instrument 1540 is prevent from being moved distally into the port P.

Figure 16:
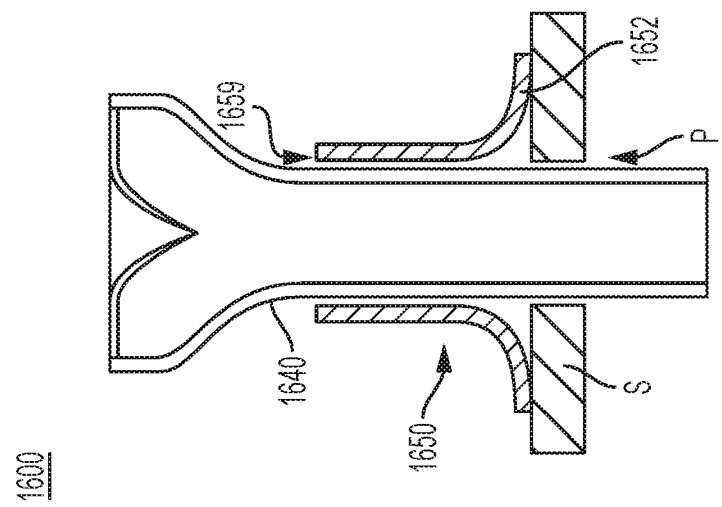
FIG. 16 is a cross-sectional illustration of a port placement guide, according to an embodiment.

FIG. 16 is a cross-sectional illustration of a port placement guide 1600. The guide 1600 includes a base 1650. The base 1650 can be the same or similar in structure and/or function to any of the bases described herein, such as the base 1550. For example, the base 1650 can include a securement element 1652, which can be the same or similar to any of the securement elements described herein, such as the securement element 352. The base 1650 can provide strain relief assistance to medical tools or instruments inserted through the base 1650 into a port P. In some embodiments, the base 1650 can seal around medical tools or instruments inserted through the base 1650 such that fluids are prevented from leaking from the port P.

The base 1650 can define a lumen 1659 through which a medical instrument, such as cannula 1640, can be inserted. The base 1650 can be disposed on a surface S of a patient in a location where the port P is intended to be created. In some embodiments, a marking element (not shown) including a tracking element can be engaged with the base 1650 to assist a tracking system in identifying the location of the port P prior to the creation of the incision. Once a port P is created in the surface S, as shown in FIG. 16, an instrument such as cannula 1640 can be inserted through the base 1650 and through the port P. The instrument 1640 can remain within the lumen 1659 and the port P and provide access to an interior of the patient for other medical instruments.

Method of Using a Port Placement Guide

In some embodiments, a port placement guide, such as any of the port placement guides described herein, can be used to assist a user (e.g., surgical staff or a surgeon) in identifying suitable or preferred port placement on the surface of a patient. Suitable or preferred port placement can be based on a variety of factors, including the locations of other existing or intended ports and the need for access to other portions of the surface of the patient during the procedure. Suitable or preferred port placement may also be identified such that collisions and interference between robotic arms and between robotic arms and other instruments are avoided. For example, this identification can be based at least in part on the size, shape, and location of a robotic arm to be associated with the port and/or a robotic arm already associated with or planned to be associated with other existing or intended ports. In some embodiments, suitable or preferred port placement can also take into account a path or trajectory that a distal end (e.g., an end effector) of a robotic arm may travel to reach a port location and/or the space occupied by each portion of the robotic arm while the distal end is manipulated to the port location. In some embodiments, suitable or preferred port placement can account for a path or trajectory that a distal end (e.g., an end effector) of every robotic arm used for a procedure may travel to reach a port location and/or the space occupied by each portion of every robotic arm while the distal end is manipulated to the port location. In some embodiments, suitable or preferred port placement can also take into account patient-specific anatomy and/or fiducials, procedure-specific needs, and individual user preferences.

In some embodiments, a computing device can be configured to determine the suitable or preferred port placements on a surface of a patient and to identify the port placement locations to a user and/or to a robotic surgical system. For example, the computing device can be a personal computer (PC), a laptop, a workstation, and/or the like disposed in a central location or distributed in multiple locations. In some embodiments, the computing device may, for example, be embodied in a control tower 130 and/or user console 120 as shown in FIG. 1. The computing device can include at least a processor and a memory. In some embodiments, the computing device can also include a display, a graphic user interface, and/or the like. The memory can be, for example, a random access memory (RAM), a memory buffer, a hard drive, a database, an erasable programmable read-only memory (EPROM), an electrically erasable read-only memory (EEPROM), a read-only memory (ROM), a solid-state drive (SSD), and/or the like. The processor can be any suitable processor configured to run and/or execute a set of instructions, for example, stored in the memory. For example, the processor can be a general-purpose processor, a Field Programmable Gate Array (FPGA), an Application Specific Integrated Circuit (ASIC), a Digital Signal Processor (DSP), a central processing unit (CPU), an accelerated processing unit (APU), a front-end processor, a graphics-processing unit (GPU), and/or the like. In some embodiments, the memory can store instructions and/or code to cause the processor to execute modules, processes, and/or functions associated with determining suitable or preferred port placement locations, defining a digital representation of the workspace including potential port placement locations, and/or displaying a digital representation of the workspace including existing or suggested port placement locations. In some embodiments, the memory can store instructions and/or code to cause the processor to execute modules, processes, and/or functions associated with determining and displaying suitable or preferred robotic arm and port pairings and robotic arm trajectories and geometries. In some embodiments, the memory can store instructions and/or code to cause the processor to execute modules, processes, and/or functions associated with registering a port placement location with a particular robotic arm and/or with manipulating a distal end of the robotic arm toward a port placement location and/or into engagement with the an instrument disposed at the port placement location.

In some embodiments, the digital representation of the workspace can be a graphical representation of the surface of the patient with marked locations that can be presented on the display of the computing device. In some embodiments, the digital representation of the workspace can be an instruction, numeric, and/or machine code representation of the surface of the patient, the actual port locations, and/or the intended or recommended (e.g., suitable and/or preferred) port placement locations. In addition, the memory can be configured to store data (e.g., in a database) such as port placement location data, patient data, procedure data, and/or data associated with recommended changes to the port placement locations, as described in further detail herein.

The computing device can receive tracking data representative of the location of a tracking element, can determine the location of a potential port placement location based on the location of the tracking element, can determine and/or calculate whether the potential port placement location is suitable or preferred, and can recommend alternative port placement locations if the potential port placement location is determined and/or calculated to be not suitable or preferred. In addition, the computing device can be configured to register a port placement location and/or a path or trajectory to a port placement location with a robotic arm. In some embodiments, the computing device can be configured to manipulate a distal end of a robotic arm toward a port placement location. In some embodiments, the computing device can be configured to manipulate a distal end of the robotic arm along a particular path or trajectory. In some embodiments, the computing device can be configured to control or guide the robotic arm with respect to certain regions in space (e.g., via the use of virtual fixtures, as further described below).

For example, in some embodiments, a user (e.g., surgical staff or a surgeon) can indicate an intended procedure to be performed on a patient using a computing device. The computing device can include a graphic user interface such that the procedure can be indicated, for example, by selecting the procedure and/or entering relevant information using the graphic user interface. The computing device can suggest one or more potential port locations to the user. For example, the computing device can suggest one or more potential port locations by displaying a potential port placement location via a graphic user interface on a monitor display, on an augmented or virtual reality headset, an image projected onto the patient, or using any other suitable display device or method. In some embodiments, the suggested potential port placement locations can represent preferred port placements or optional port placement locations based on any suitable factors such as, for example, the needs of the particular procedure, prior procedure port placement layouts, and/or surgeon preferences. In some embodiments, the suggested potential port placement locations can be presented to the user in relation to anatomical landmarks of the patient. In some embodiments, a user can additionally or alternatively approximate potential port placement locations based on, for example, user knowledge and/or experience.

The user can obtain a port placement guide, such as any of the port placement guides described herein. For example, the user can remove the port placement guide from associated packaging and/or assemble the port placement guide. The user can couple the port placement guide to the patient (e.g., a surface of the patient) at a potential port placement location. The computing device can be communicatively coupled to or include a tracking system such that the location of a tracking element of the port placement guide can be observed and/or determined. In some embodiments, the user can pivot a portion of the guide having the tracking element, such as a member of the guide relative to a base of the guide, such that the tracking system can receive additional location and/or orientation data for analysis by the computing device. The computing device can then use the location of the tracking element to identify the location of the port placement guide on the surface of the patient. The computing device can then analyze whether the location of the port placement guide is suitable or preferred, as further described below. If the location is suitable or preferred, the computing device can indicate (e.g., using a graphic user interface) to the user that the port placement guide is in a suitable or preferred location.

If the computing device determines that the port placement guide is not in a suitable or preferred location for a port to be created, the computing device can suggest to the user that the port placement guide be moved to an alternative location. In some embodiments, the computing device can suggest the alternative location. The user can adjust the location of the port placement guide based on the feedback received from the computing device. For example, if the computing device indicates that a first port placement location may be unsuitable to the procedure, the user can move the guide to a second port placement location. The computing device can then analyze whether the second port placement location is suitable or preferred based on, for example, data received indicating the location of the tracking element. The steps of moving the port placement guide and analyzing the suitability of the location can be repeated until the computing device confirms that the location of the port placement guide on the surface of the patient (and thus the port location) is suitable.

Any suitable number of port placement guides can be used to identify any number of port locations. In some embodiments, rather than using an additional guide, the same guide can be used to determine each of the port placement locations for a procedure. For example, after determining that a particular port location is suitable, the guide or a user can mark the surface of the patient in the particular port location. The guide can then be moved to a second potential port placement location to determine the suitability of the second potential port placement location.

After determining two or more port placement locations using the computing device, the computing device can compare all confirmed and/or remaining unconfirmed port placement locations for their suitability relative to one another, relative to a surgical table, and/or relative to the patient's position on the surgical table. The computing device may then recommend one or more guides or port placement locations be repositioned such that, for example, the workspace is transitioned to a preferred arrangement and/or potential collisions between surgical staff and/or robotic arms during the procedure are minimized or avoided.

The one or more port placement locations can be finalized and logged by the computing device (e.g., logged into software associated with a graphic user interface). A model (e.g., digital representation) of the workspace can be generated and/or finalized including intended robotic arm and port pairing assignments. Each port placement location can be registered with a robotic arm such that the robotic arm can be manipulated toward a particular port placement location, as described below. In some embodiments, at least one particular path or trajectory for each robotic arm toward the port placement location can be generated such that, for example, the workspace is transitioned to a preferred arrangement and risk of collisions between surgical arms is reduced. The computing device can provide instructions to the user to dock specific robotic arms to specific ports. The instructions can be based on a pre-operative plan and/or the generated model.

An incision can be made at a final port location to create a port and a cannula can be inserted into the port. In some embodiments, the cannula can include a cannula docking feature (e.g., clamp, snap, or other suitable mount or docking feature). The distal end of the robotic arm registered to the port can be manipulated (e.g., manually by a user, and/or automatically and/or assistively by a control system as described below) and coupled to the cannula at the port via the cannula docking feature. Alternatively, the distal end of the robotic arm may be coupled to the cannula, and then the arm and cannula assembly may together be manipulated toward the port (e.g., manually, automatically, and/or assistively as described below), where the cannula can thereafter be inserted into the port.

In some embodiments, a port placement guide, such as any of the guides described herein, can be configured to couple to a portion of a robotic arm (e.g., to act as a simulated cannula). For example, a port placement guide can include a guide docking feature (e.g., clamp, snap, or other suitable mount or docking feature) configured to couple to a distal end of a robotic arm. The guide docking feature may be disposed on the member, marking element, base, or any suitable portion of the port placement guide. Accordingly, the robotic arm can move the guide to, for example, simulate the behavior of the robotic arm and/or a cannula if the robotic arm were to be attached to a cannula positioned in a port located where the guide is placed (e.g., preliminary port location). In some embodiments, a port placement guide having a guide docking feature can be used, for example, for training a user and/or planning a procedure.

In some embodiments, the distal end of the robotic arm can be moved to the cannula docking feature manually by a user. As further described below with reference to FIGS. 18A and 18B, a control system may guide manual movements of the distal end of the robotic arm toward the port by, for example, adjusting various torques of the robotic arm in accordance with one or more virtual fixtures. In some embodiments, a control system may additionally or alternatively control the robotic arm to automatically follow a predetermined, generated path or trajectory toward the port. It should be understood that in some embodiments, the robotic arm may be manipulated in any suitable combination of manners (e.g., completely manually, automatically by a control system, assistively by a control system, etc.) during different portions of its movement toward the port. In some embodiments, when the robotic arm reaches the final location, the robotic arm can automatically prevent any further movement and can maintain the final position. The user can then engage the distal end of the robotic arm (e.g., an arm docking feature located at the distal end) with the docking feature of the cannula by, for example, moving the cannula to the distal end of the robotic arm. In some embodiments, after docking the robotic arm to the cannula, the user can reposition the robotic arm as needed to, for example, transition the positioning or pose of the robotic arm to a preferred position or pose relative to the workspace and/or other robotic arms.

FIGS. 17A-17E illustrate an exemplary method of using a port placement guide, such as any of the port placement guides described herein. As shown in FIG. 17A, a user can identify a desired port placement location L on the surface S (e.g., a body wall such as the skin) of a patient. As shown in FIG. 17B, the user can then obtain a port placement guide 1700. The port placement guide 1700 can be the same or similar to any port placement guide described herein. For example, the port placement guide 1700 can include a base 1750, a member 1760, a flexible joint 1762, and a marker element 1780. The marker element 1780 can include a tracking assembly 1772. As represented by 1700', the user can couple the port placement guide 1700 to the surface S at the desired port placement location L. A tracking device 1790 can be arranged such that the tracking device 1790 can detect the location of the tracking assembly 1772.

As shown in FIG. 17C, the member 1760 of the guide 1700 can be pivoted relative to the base 1750 (and, thus, relative to the location L) over any suitable range in any suitable direction (e.g., through the range of motion of the flexible joint 1762). For example, the member 1760 can be pivoted such that the guide 1700 is in a second position represented in phantom by 1700' and in a third position represented in phantom by 1700". The tracking device 1790 can detect the position and/or orientation of the tracking element 1772 at each of these locations. In some embodiments, a processor (not shown) associated with the tracking device 1790 can process the location and/or orientation data (e.g., tracking data) collected by the tracking device 1790 and determine the location L of the guide 1700 on the surface S. For example, the processor can fit the tracking data to a spherical surface 1792 disposed on the surface S, as shown in FIG. 17D. The center of the sphere having the spherical surface 1792 can be identified (e.g., by the processor) as the location L, which can also be identified as an entrance point to a potential port P.

Additionally, in some embodiments, a three-dimensional workspace for a tool can be calculated. For example, if a particular catheter is intended to be inserted through the port P, a three-dimensional workspace can be calculated for the catheter, including a predicted movement area of the catheter above the surface S during use of the catheter. The three-dimensional workspace calculated for a particular tool can be incorporated into the analysis of the suitability of a port placement location by, for example, any of the devices or methods described herein.

The method shown and described with respect to FIGS. 17A-17D can be performed multiple times to identify multiple port locations. For example, after identifying the location of the potential port P, the guide 1700 can be moved to a second desired port placement location and pivoted such that the tracking device 1790 can collect tracking data associated with the second desired port placement location. A second potential port $P_2$ can then be identified, as shown in FIG. 17E. These steps can be repeated multiple times such that a third potential port $P_3$ and a fourth potential port $P_4$ are also identified on the surface S of a patient. Although FIG. 17E depicts four potential port locations being identified, it should be understood that the method can be used to identify fewer (e.g., one, two, or three) or more ports (e.g., five, six, or more).

When a potential port location has been identified as a suitable or preferred port location, the port location can be registered to one or more robotic arms (e.g., such that the one or more robotic arms can be guided toward the port location). For example, in some embodiments, the coordinates of the potential port P on the surface S can be converted to a data format relatable to robotic arms (e.g., by the processor) such that the coordinates can be registered to a robotic arm for use in guiding the robotic arm toward the potential port P. In some embodiments, a distal end of a robotic arm can be moved toward a port location registered to the robotic arm. In some embodiments, the distal end of a robotic arm can be coupled to a medical instrument (e.g., a cannula or trocar), and the robotic arm can be manipulated such that the medical instrument is, for example, moved into engagement with the surface of the patient at the location of the potential port location or moved into a cannula or port placement guide previously positioned at the port location.

Figure 18B:
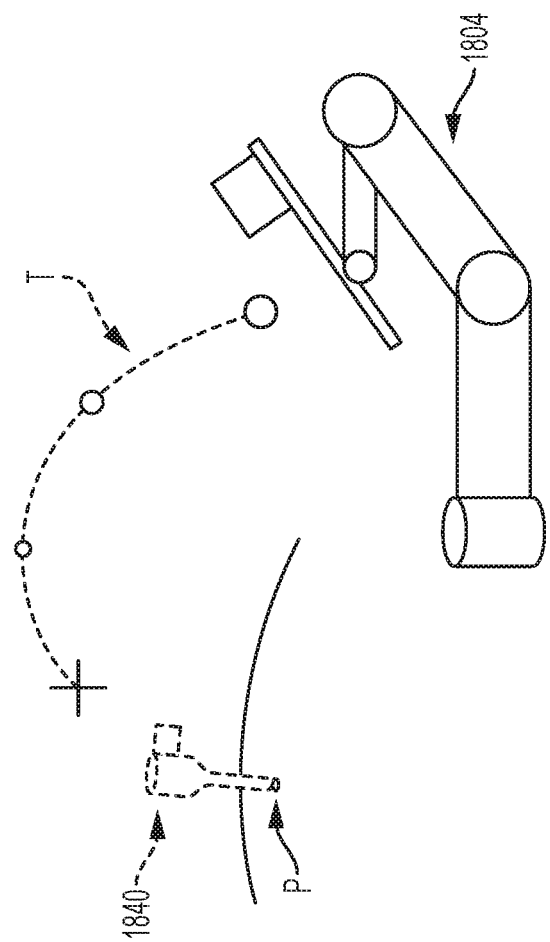
FIG. 18B illustrates a robotic arm in a second configuration coupled to the cannula at a port location on a patient, according to an embodiment.
Figure 18A:
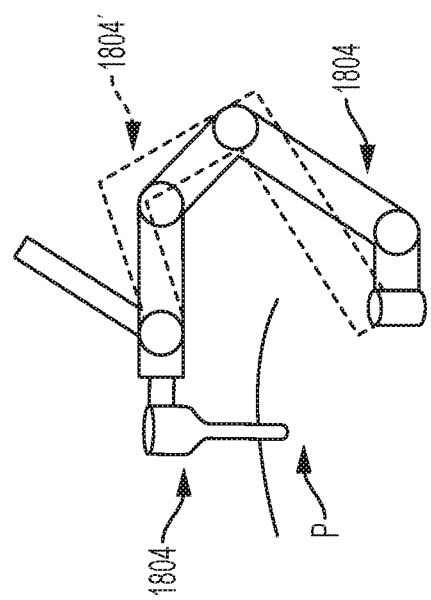
FIG. 18A illustrates a robotic arm in a first configuration uncoupled from a cannula at a port location on a patient, according to an embodiment.

As a specific example, FIGS. 18A and 18B illustrate a cannula 1840 and a robotic arm 1804 in a first uncoupled configuration and a second coupled configuration, respectively. The cannula 1840 can be disposed in a port P that has been registered to a robotic arm 1804. In some embodiments, the robotic arm 1804 can be guided to the cannula 1840 along a path or trajectory T, as shown in FIG. 18A. In some embodiments, the robotic arm 1804 can be automatically driven along at least part of a predetermined trajectory T to the cannula 1840 or the port P using a suitable control algorithm. In some embodiments, the robotic arm 1804 can be moved manually toward the cannula 1840 or the port P by a user. Such manual movement may be assisted by a suitable control system to, for example, provide gravity compensation and/or friction compensation to aid the manual movement of the robotic arm 1804. Suitable exemplary gravity compensation and friction compensation algorithms are described in further detail in U.S. application Ser. No. 15/838,094 titled "ACTIVE BACKDRIVING FOR A ROBOTIC ARM" and filed on Dec. 11, 2017, which is hereby incorporated in its entirety by this reference.

As another example, a control system may help guide the movement of the robotic arm via one or more virtual fixtures, which may substantially prevent the arm from being moved into one or more defined regions or constrain the arm within one or more defined regions (e.g., between the starting position of the robotic arm 1804 and the cannula 1840 or the port P). For example, one or more virtual fixtures can be defined to represent one or more regions in which the robotic arm 1804 does not interfere with access to any additional ports or the robotic arm paths to those ports. In some variations, the robotic arm 1804 may be guided to the location of the port P via guidance with one or more virtual fixtures constraining movement of the robotic arm 1804 (e.g., task space virtual fixtures applied to the arm, joint space virtual fixtures applied on a joint-by-joint level of the arm, etc.). Such virtual fixtures may include, for example, a guiding virtual fixture or a forbidden regions virtual fixture.

In some variations, as described herein, a virtual fixture may be defined as a set of one or more boundaries for the robotic arm 1804, such that the movement of the robotic arm 1804 (or selected points thereon) is substantially constrained relative to the boundaries. For example, a user may manually manipulate and position the robotic arm 1804 (e.g., with actuated assistance provided by gravity compensation and/or friction compensation control modes). In a guiding virtual fixture, a control system (e.g., any control system or suitable computing device described herein) may generally permit such user-manipulated motion of the robotic arm 1804 within the boundaries of the virtual fixture, while substantially preventing or discouraging motion outside of the boundaries. For example, motion outside of the boundaries may be resisted by delivering a set of one or more resistance joint torques opposing one or more force components that are perpendicular to the reference plane (any force component that tends to cause a portion of the robotic arm 1804 to move outside of the reference plane). The control system may drive one or more of the joints in the robotic arm 1804 to deliver the resistance joint torque in accordance with the virtual fixture. In a forbidden regions virtual fixture, the system may generally permit user-manipulated motion of the robotic arm 1804 outside of the set of the set of boundaries of the virtual fixture, while substantially preventing or discouraging motion inside the boundaries.

In yet other variations, movement of at least a portion of the robotic arm 1804 may be guided in a trajectory following mode to the location of the port P. In the trajectory following mode, the robotic arm 1804 may move to follow a sequence of one or more trajectory (e.g., Cartesian trajectory) commands. Trajectory commands may include, for example, velocity commands (framed in terms of linear and/or angular movement) or target pose commands (framed in terms of end objective position and orientation of the links and joint modules. If the command is a target pose that requires a number of link movements to transition from a current pose to the target pose, then the control system may generate a trajectory defining the necessary link movement. If the command relates to a target pose that is the same as the current pose, then the control system may generate trajectory commands effectively resulting in a commanded "hold" position. For instance, the trajectory may be based on inputs including: commanded velocities or poses (e.g., transformation matrix, rotation matrix, 3D vector, 6D vector, etc.), the arm links to be controlled, measured joint parameters (angles, velocities, accelerations, etc.), tool parameters (type, weight, size, etc.), and environmental parameters (e.g., predefined regions which the arm link is barred or forbidden from entering, etc.). The control system may then use one or more algorithms to generate the outputs of commanded joint parameters (position, velocity, acceleration, etc.) to the firmware and/or commanded motor currents as current feedforward to the firmware. Suitable algorithms for determining these output commands include algorithms based on forward kinematics, inverse kinematics, inverse dynamics, and/or collision avoidance (e.g., collision between arm links, between different instances of the robotic arm, between the arm and environment, etc.).

As shown in FIG. 18B, a pose or geometry of the robotic arm 1804 in the second configuration can be modeled and/or transitioned to a preferred pose or geometry. For example, the pose or geometry of the robotic arm 1804 can be selected such that portions of the robotic arm 1804 (e.g., links and/or joints) are not blocking access to other ports on the surface of the patient. As represented in FIG. 18B, after the robotic arm 1804 has reached the cannula 1840, for example, a pose 1804' of the robotic arm 1804 can be identified. The robotic arm 1804 can then be transitioned to the pose 1804' for the remainder of the procedure.

In some embodiments, the distal end of the robotic arm 1804 can be coupled to a medical instrument (e.g., a cannula 1840 or trocar), and the robotic arm can be manipulated such that the medical instrument is, for example, moved into engagement with the surface of the patient at the location of the potential port location or moved into a cannula or port placement guide previously positioned at the port location. For example, a port placement guide, such as any of the guides described herein, can be positioned on the surface of the patient. The robotic arm 1804 can be engaged with a docking feature of a medical instrument. The robotic arm 1804 can then be manipulated such that the medical instrument is maneuvered into engagement with or through a lumen of the guide positioned on the surface of the patient and into contact with the surface of the patient and/or into the port.

Figure 19A:
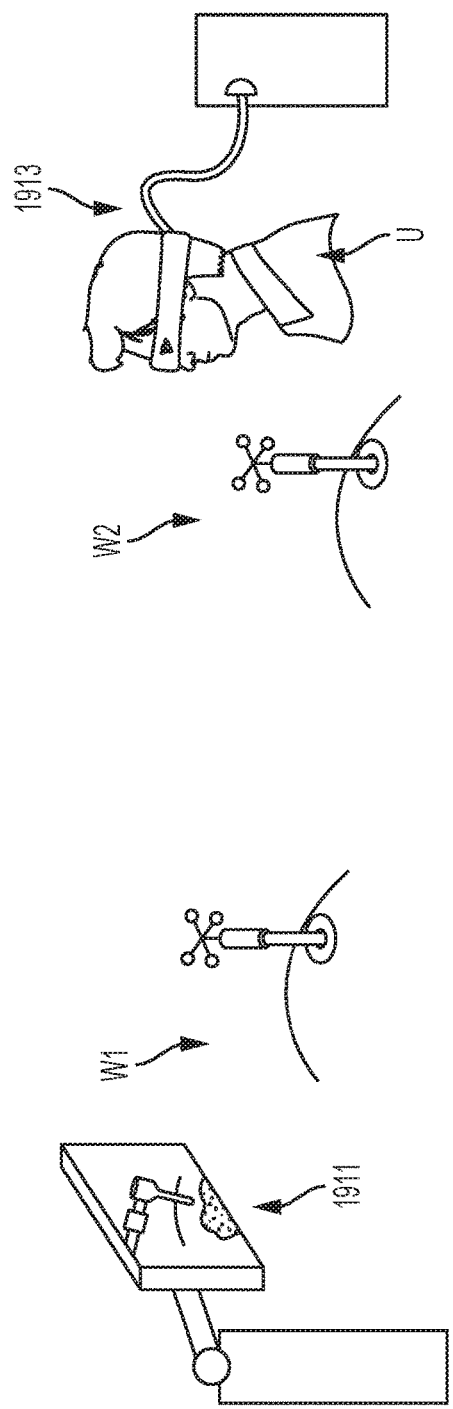
FIGS. 19A-19C illustrate various manners of communicating a workspace to a user, according to various embodiments.
Figure 19B:
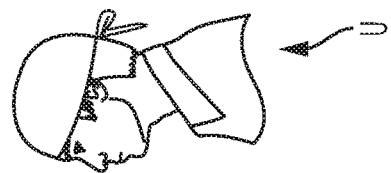
Figure 19C:
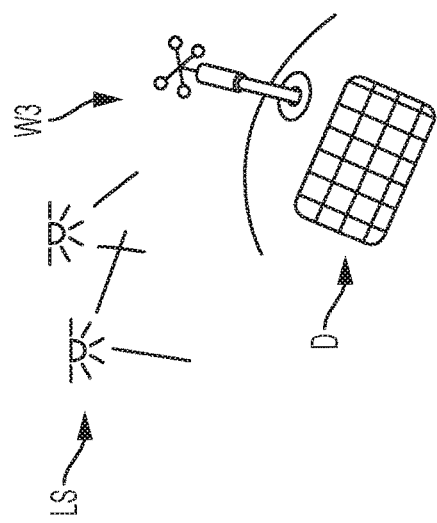

As shown in FIGS. 19A-19C, a three-dimensional workspace for an intended medical instrument and/or a robotic arm can be displayed or communicated to a user through various graphical rendering means. For example, as shown in FIG. 19A, a workspace W1 can by communicated to a user via a computer monitor 1911. The workspace W1 can include, for example, any of the port placement guides described herein.

As shown in FIG. 19B, in some embodiments, a workspace W2 can be communicated to a user U via a headset 1913. The headset 1913 can be an augmented reality or a virtual reality headset. A port placement guide, such as any of the port placement guides described herein, can be positioned on a surface of a patient. The location of the port placement guide can be detected via any of the methods described herein. The user U can visualize the workspace W2 associated with the location of the port placement guide using the headset 1913.

As shown in FIG. 19C, in some embodiments, a workspace W3 can be communicated to a user U via light or lasers projected to form a pattern or indicator directly on a surface of a patient. The light or lasers can be projected from a light source LS. For example, the lights or lasers can be projected onto a surface to identify an area D. The area D may be associated with a procedure or an action the user U is to take. For example, the area D may represent a suggested alternative location for the placement of a port placement guide, such as any of the guides described herein.

Figure 20:
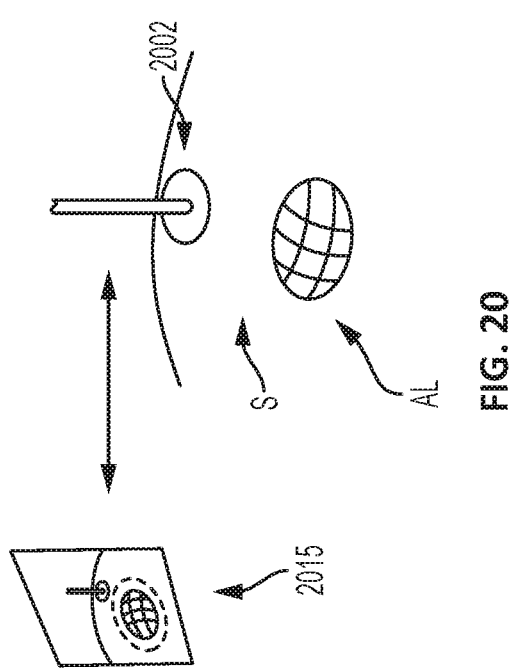
FIG. 20 illustrates a method in which a predicted workspace can be compared to a pre-operative model, according to an embodiment.

In some embodiments, as shown in FIG. 20, a predicted workspace can be compared to a pre-operative model. For example, a computing device, such as any of the computing devices described herein, can generate a pre-operative model of a surface S of the patient including potential port placement locations. After a user has placed one or more port placement guides 2002, such as any of the guides described herein, on the surface S of a patient, the computing device can generate a predicted workspace (shown on display 2015) based, at least in part, on data received from tracking elements from the one or more port placement guides. The computing device can then compare the predicted workspace to the pre-operative model and any differences between the predicted workspace and the pre-operative model can be identified. The user and/or the computing device can then determine whether to modify the final workspace layout based on the pre-operative model or to accept the predicted workspace. For example, the computing device can identify a recommended alternative port placement location AL on the surface S.

In some embodiments, pre-procedure data, intra-procedure data, and/or post-procedure data can be used to generate the pre-operative model or to recommend adjustments to a port placement location or a predicted workspace. For example, intra-procedure data or post-procedure data gathered based on a previous procedure of the same patient or from previous procedures of different procedures can be incorporated into the analysis. This data can be used to refine algorithms used to predict, analyze, and confirm port placement locations.

Figure 21A:
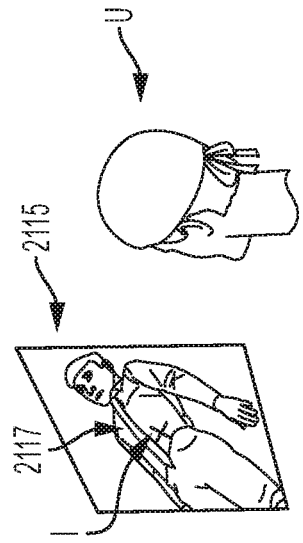
FIGS. 21A and 21B illustrate a method of combining data gathered by a tracking system with patient positioning information to identify a port location, according to an embodiment.
Figure 21B:
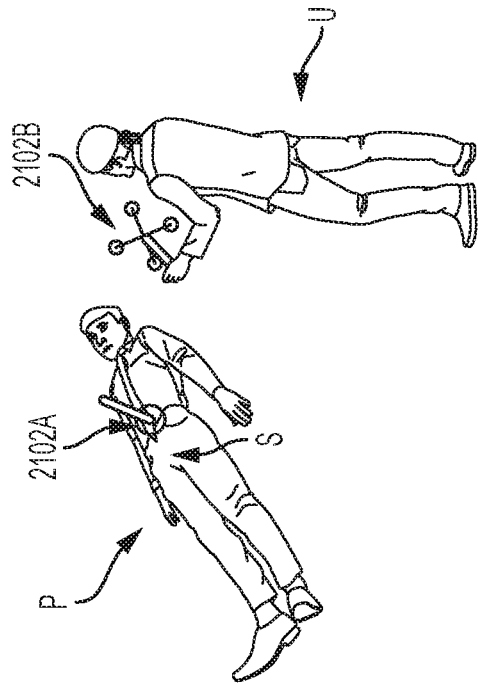

In some embodiments, data gathered by a tracking system can be combined with patient positioning information. FIGS. 21A and 21B illustrate a user U using a system including a display 2115 and a number of port placement guides (2102A and 2102B). The port placement guides can be the same and/or similar in structure and/or function to any of the guides described herein. As shown in FIG. 21B, the user can position a port placement guide 2102A on the surface S of a patient P. As shown in FIG. 21A, the user can via the position of the guide 2102A represented as indicator I on a representation of the patient 2117. The representation of the patient 2117 can be generated based on, for example, patient positioning information. In some embodiments, tracking data associated with the guide 2102A can be combined via the use of a graphical user interface on the display 2115 such that the user can input data including the patient positioning information. For example, the user can move, scale, and/or orient a graphical representation of a patient relative to a graphical representation of a port on a screen. The user can also identify patient fiducials, such as indicating the location of the head, feet, arms, and other anatomical parts, and their locations relative to a port placement guide. Additionally, the user can map the surface of a patient using one or more port placement guide or using a three dimensional scan. The patient model can then be automatically defined from the inputted data. The patient model can be confirmed or modified by the user. Additional port placement guides, such as guide 2102B, may be placed relative to other guides such as guide 2102A.

Figure 22:
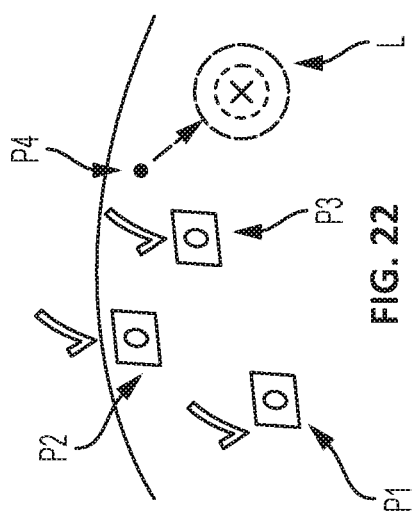
FIG. 22 is a perspective view illustration of a workspace including potential port placement locations, according to an embodiment.

In some embodiments, as shown in FIG. 22, multiple port placements can be compared to pre-operative plans or a procedure guide. A user can be provided with suggestions for improved port placement based on any suitable factors, such as any of the various factors described herein. As shown in FIG. 22, four potential port placement locations P1-P4 can be identified using, for example, a port placement guide, such as any of the port placement guides described herein. The user could then be provided with a recommendation that one of the potential port placement locations (e.g., P4) be moved to a different location L.

Figure 23B:
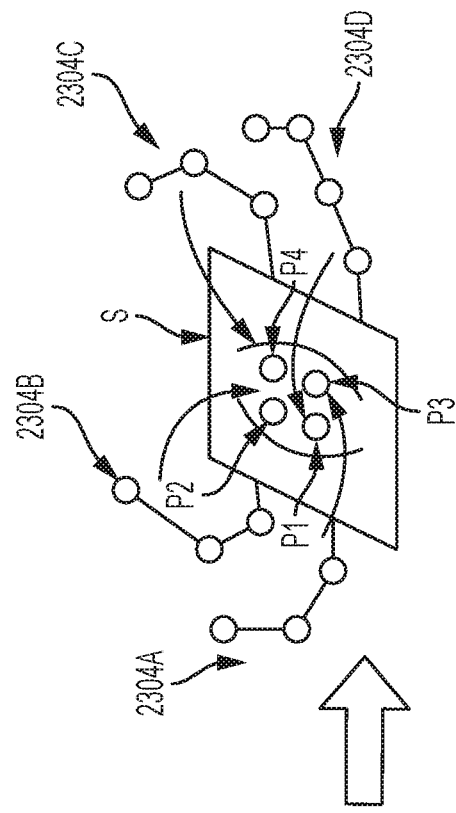
FIG. 23B is an illustration of four robotic arms arranged relative to a workspace including four pour placement locations, according to an embodiment.
Figure 23A:
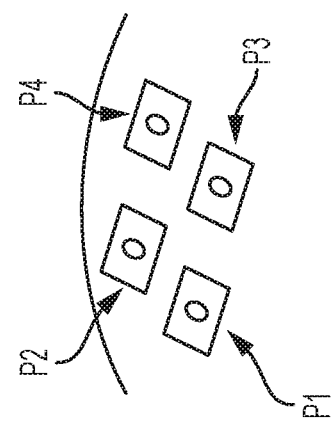
FIG. 23A is an illustration of a workspace including four port placement locations, according to an embodiment.

In some embodiments, as shown in FIGS. 23A and 23B, an arm position can be generated for each identified port location. For example, FIG. 23A shows four port placement locations P1-P4. A model of the eventual robotic arm positions within the workspace relative to the port placement locations can be generated. The generated model can, for example, include preferred pairing assignments between robotic arms and port placement locations, preferred robotic arm positions, and preferred paths or trajectories to the port placement locations. The preferred pairing assignments, robotic arm positions, and/or robotic arm paths or trajectories can be identified for any suitable goal, such as to minimize collisions, to maximize user access to particular regions of the patient, and/or based on outcomes/data from previous surgeries. The pairing assignments can then be communicated to the user. As shown in FIG. 32B, each robotic arm of robotic arms 2304A-2304D can then be manipulated toward a respective port placement location (e.g., one of port placement locations P1-P4) on a surface S of the patient. In some embodiments, the model can also provide a recommended order of events such that the robotic arms are moved in sequence toward each port placement location.

Figure 24:
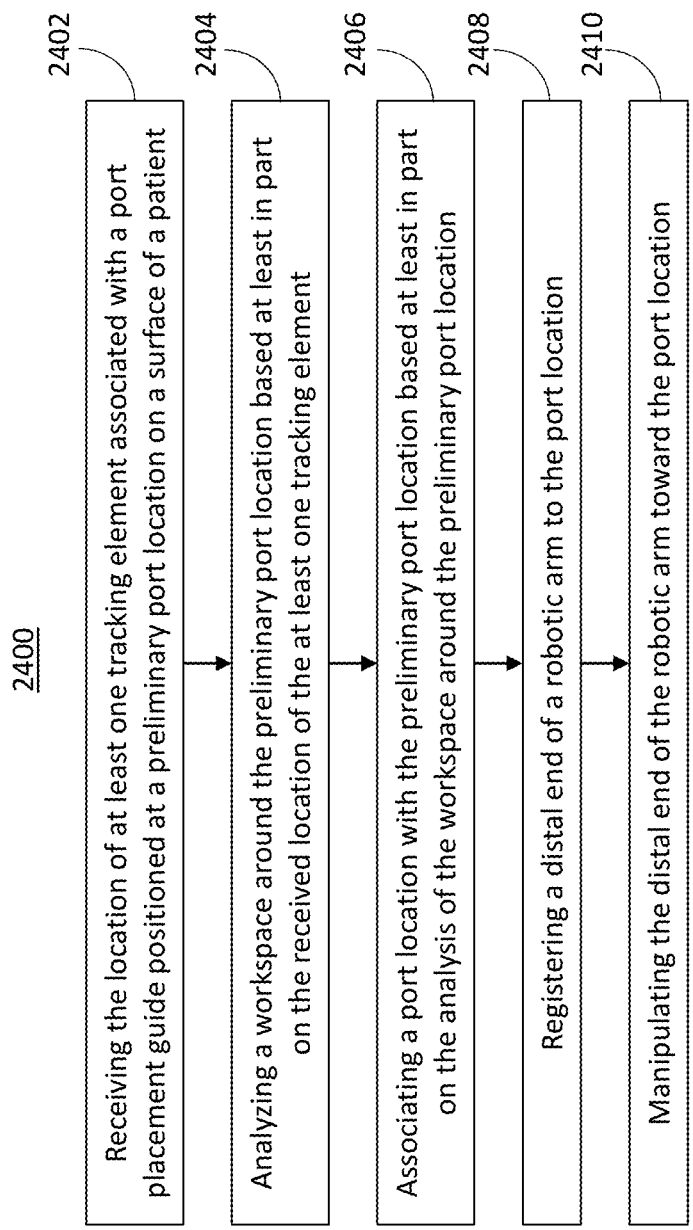
FIG. 24 is a flow chart of a method, according to an embodiment.

FIG. 24 is a flow chart of a method 2400, according to an embodiment. The method 2400 can include receiving the location of at least one tracking element associated with a port placement guide positioned at a preliminary port location on a surface of a patient, at 2402. A workspace around the preliminary port location can be analyzed based at least in part on the received location of the at least one tracking element, at 2404. In some embodiments, the analyzing can include assessing the preliminary port location relative to at least one of an anatomical feature of the patient and an access location associated with an intended procedure. In some embodiments, the analyzing can include assessing at least one of a location of a second robotic arm, the location of a second preliminary port location, and the location of a second port location. A port location can be associated with the preliminary port location based at least in part on the analysis of the workspace around the preliminary port location, at 2406. A distal end of a robotic arm can be registered to the port location, at 2408. The distal end of the robotic arm can be manipulated toward the port location, at 2410. In some embodiments, manipulating the distal end of the robotic arm can include automatically controlling the robotic arm via a trajectory following algorithm. In some embodiments, manipulating the distal end of the robotic arm can include assistively controlling the robotic arm via one or more virtual fixtures. In some embodiments, a second location associated with the port placement guide positioned at a second preliminary port location on a surface of a patient can be received.

Figure 25:
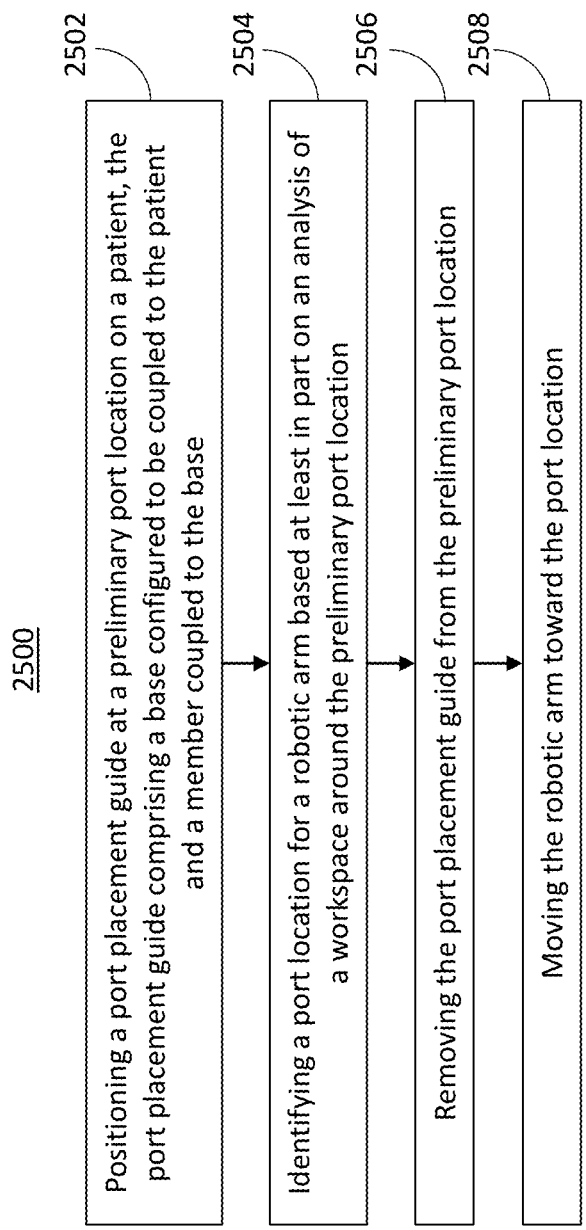
FIG. 25 is a flow chart of a method of using a port placement guide, according to an embodiment.

FIG. 25 is a flow chart of a method 2500 of using a port placement guide, according to an embodiment. The method 2500 can include positioning a port placement guide at a preliminary port location on a patient, at 2502. The port placement guide can be the same or similar in structure and/or function to any of the port placement guides described herein. For example, the port placement guide can include a base configured to be coupled to the patient, and a member coupled to the base. A port location for a robotic arm can be identified based on an analysis of a workspace around the preliminary port location, at 2504. The port placement guide from the preliminary port location can be removed, at 2506. The robotic arm can be moved toward the port location, at 2508. In some embodiments, the port placement guide can be repositioned at a second preliminary port location and the second preliminary port location can be identified as the port location. In some embodiments, an incision can be created at the port location. A medical instrument (e.g., a cannula) can be at least partially inserted through the port location. The distal end of the robotic arm can be coupled to the medical instrument. In some embodiments, the patient surface at the port location can be marked via axially translating a marking element through a lumen defined by the port placement guide.

While various embodiments have been described above, it should be understood that they have been presented by way of example only, and not limitation. Where methods described above indicate certain events occurring in certain order, the ordering of certain events may be modified. Additionally, some of the events may be performed concurrently in a parallel process when possible, as well as performed sequentially as described above.

In some embodiments, the systems (or any of its components) described herein can include a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Although various embodiments have been described as having particular features and/or combinations of components, other embodiments are possible having a combination of any features and/or components from any of the embodiments where appropriate.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. An apparatus comprising:
a base configured to couple to a patient at a preliminary port location for a robotic arm;
a member coupled to the base and comprising a first end and a second end opposite the first end, the member being transitionable between an extended configuration and a compressed configuration;
at least one tracking element coupled to the member, wherein the at least one tracking element is configured to allow tracking of the member relative to the preliminary port location; and
a marking element engaged with the member, such that when the base is coupled to the patient, the marking element is spaced apart from the patient when the member is in the extended configuration and the marking element is in contact with the patient when the member is in the compressed configuration.

2. The apparatus of claim 1, wherein the base is configured to be coupled to the patient via at least one of suction or an adhesive material.

3. The apparatus of claim 1, wherein the member is coupled to the base via a flexible joint, the flexible joint being configured such that the member is pivotable relative to the base.

4. The apparatus of claim 1, wherein the member is rotationally fixed relative to the base.

5. The apparatus of claim 1, wherein the at least one tracking element is disposed on the second end of the member, the first end of the member disposed a first distance from the base and the second end of the member being disposed a second distance greater than the first distance from the base.

6. The apparatus of claim 1, wherein the at least one tracking element comprises infrared reflective material.

7. The apparatus of claim 1, wherein the at least one tracking element comprises an electromagnetic transmitter.

8. The apparatus of claim 1, wherein the at least one tracking element comprises a plurality of tracking elements arranged in a pattern.

9. The apparatus of claim 1, wherein the base and the member collectively define a lumen such that, when the base is disposed on the patient, the marking element can be inserted through the lumen to contact the patient.

* * * * *